US006117167A

United States Patent [19]
Goicoechea et al.

[11] Patent Number: 6,117,167
[45] Date of Patent: Sep. 12, 2000

[54] ENDOLUMINAL PROSTHESIS AND SYSTEM FOR JOINING

[75] Inventors: George Goicoechea, Freeport, Bahamas; John Hudson, Glenfield, United Kingdom; Claude Mialhe, Draguignan, France; Andrew H. Cragg, Edina, Minn.; Michael D. Dake, Stanford, Calif.

[73] Assignee: Boston Scientific Technology, Inc., Maple Grove, Minn.

[21] Appl. No.: 09/020,749

[22] Filed: Feb. 9, 1998

Related U.S. Application Data

[63] Continuation of application No. 08/461,513, Jun. 5, 1995, Pat. No. 5,716,365, and a division of application No. 08/317,763, Oct. 4, 1994, Pat. No. 5,609,627, which is a continuation-in-part of application No. 08/312,881, Sep. 27, 1994.

[30] Foreign Application Priority Data

Feb. 9, 1994 [EP] European Pat. Off. .............. 94400284
Jun. 10, 1994 [EP] European Pat. Off. .............. 94401306

[51] Int. Cl.[7] ...................................................... A61F 2/00
[52] U.S. Cl. .............................................................. 623/1.16
[58] Field of Search .................................. 623/1, 11, 12, 623/1.16

[56] References Cited

U.S. PATENT DOCUMENTS

| | | | |
|---|---|---|---|
| 3,657,744 | 4/1972 | Ersek | ......................................... 623/11 |
| 3,868,956 | 3/1975 | Alfidi et al. . | |
| 3,878,565 | 4/1975 | Sauvage . | |
| 3,890,977 | 6/1975 | Wilson . | |
| 3,996,938 | 12/1976 | Clark, III . | |
| 4,140,126 | 2/1979 | Choudhury . | |
| 4,149,911 | 4/1979 | Clabburn . | |
| 4,214,587 | 7/1980 | Sakura, Jr. . | |
| 4,306,318 | 12/1981 | Mano et al. . | |
| 4,425,908 | 1/1984 | Simon . | |
| 4,503,569 | 3/1985 | Dotter . | |
| 4,512,338 | 4/1985 | Balko et al. . | |

(List continued on next page.)

FOREIGN PATENT DOCUMENTS

| | | |
|---|---|---|
| 0145166B1 | 6/1985 | European Pat. Off. . |
| 0423916A1 | 4/1991 | European Pat. Off. . |
| 0 464 755 A1 | 1/1992 | European Pat. Off. . |
| 0 480 667 A1 | 4/1992 | European Pat. Off. . |

(List continued on next page.)

OTHER PUBLICATIONS

Dotter et al., "Transluminal Expandable Nitinol Coil Stent Grafting: Preliminary Report", Technical Developments and Instrumentation, *Radiology*, vol. 147, pp. 259–260 (Apr. 1983).
Schetky, "Shape Memory Alloys", pp. 74–82.
K. Otsuka et al., "Shape–Memory Alloys–Pseudoelasticity", *Metals Forum*, vol. 4, No. 3, pp. 142–152 (1981).
Cragg et al., "Nonsurgical Placement of Arterial Endoprostheses: A New Technique Using Nitinol Wire", *Radiology*, vol. 147, No. 1, pp. 261–263 (Apr. 1983).
Cragg et al., "Percutaneous Arterial Grafting", *Radiology*, vol. 150, No. 1, pp. 45–49 (1984).
T. W. Duerig et al. "An Engineer's Perspective Pseudoelasticity", pp. 369–393.
Cragg et al., "Stends/Vascular Stents", *Interventional Radiology*, pp. 686–692 (1990.

*Primary Examiner*—Michael J. Milano
*Attorney, Agent, or Firm*—Ratner & Prestia

[57] ABSTRACT

A stent joining means is provided for joining a first endoluminal stent to a second endoluminal stent to define a continuous lumen through the first and second endoluminal stents. The stent joining means includes two transversely spaced female portions on the first endoluminal stent. The stent joining means also includes a male engaging portion of the second endoluminal stent. The male engaging portion is configured to be entered into one of the female portions in a radially compressed state and thereafter expanded in the female portion such that an outer surface of the male engaging portion and an inner surface of the female portion are interengaged to resist longitudinal movement to prevent separation of the first and second endoluminal stents in service.

82 Claims, 23 Drawing Sheets

U.S. PATENT DOCUMENTS

| | | |
|---|---|---|
| 4,553,545 | 11/1985 | Maass et al. . |
| 4,560,374 | 12/1985 | Hammerslag . |
| 4,562,596 | 1/1986 | Kornberg . |
| 4,577,631 | 3/1986 | Kreamer . |
| 4,580,568 | 4/1986 | Gianturco . |
| 4,617,932 | 10/1986 | Kornberg . |
| 4,649,922 | 3/1987 | Wiktor . |
| 4,655,771 | 4/1987 | Wallsten . |
| 4,665,906 | 5/1987 | Jervis . |
| 4,665,918 | 5/1987 | Garza et al. . |
| 4,681,110 | 7/1987 | Witkor . |
| 4,728,328 | 3/1988 | Hughes . |
| 4,729,766 | 3/1988 | Bergentz et al. . |
| 4,732,152 | 3/1988 | Wallsten et al. . |
| 4,733,665 | 3/1988 | Palmaz . |
| 4,739,762 | 4/1988 | Palmaz . |
| 4,762,128 | 8/1988 | Rosenbluth . |
| 4,768,507 | 9/1988 | Fischell et al. . |
| 4,772,264 | 9/1988 | Cragg . |
| 4,776,337 | 10/1988 | Palmaz . |
| 4,800,882 | 1/1989 | Gianturco . |
| 4,820,298 | 4/1989 | Leveen et al. . |
| 4,830,003 | 5/1989 | Wolff et al. . |
| 4,856,516 | 8/1989 | Hillstead . |
| 4,878,906 | 11/1989 | Lindemann et al. . |
| 4,886,062 | 12/1989 | Wiktor . |
| 4,886,065 | 12/1989 | Collins, Jr. . |
| 4,913,141 | 4/1990 | Hillstead . |
| 4,922,905 | 5/1990 | Strecker . |
| 4,969,458 | 11/1990 | Wiktor . |
| 4,969,890 | 11/1990 | Sugita et al. . |
| 4,994,071 | 2/1991 | MacGregor . |
| 5,019,085 | 5/1991 | Hillstead . |
| 5,019,090 | 5/1991 | Pinchuk . |
| 5,035,706 | 7/1991 | Gianturco . |
| 5,037,427 | 8/1991 | Harada et al. . |
| 5,041,126 | 8/1991 | Gianturco . |
| 5,047,050 | 9/1991 | Arpesani . |
| 5,057,092 | 10/1991 | Webster, Jr. . |
| 5,064,435 | 11/1991 | Porter ................................... 606/198 |
| 5,067,957 | 11/1991 | Jervis . |
| 5,078,726 | 1/1992 | Kreamer . |
| 5,078,736 | 1/1992 | Behl . |
| 5,085,635 | 2/1992 | Cragg . |
| 5,104,399 | 4/1992 | Lazarus . |
| 5,104,404 | 4/1992 | Wolff . |
| 5,123,917 | 6/1992 | Lee . |
| 5,133,732 | 7/1992 | Wiktor . |
| 5,135,536 | 8/1992 | Hillstead . |
| 5,151,105 | 9/1992 | Kwan-Gett . |
| 5,161,547 | 11/1992 | Tower . |
| 5,183,085 | 2/1993 | Timmermans . |
| 5,192,297 | 3/1993 | Hull . |
| 5,201,901 | 4/1993 | Harada et al. . |
| 5,207,695 | 5/1993 | Trout . |
| 5,236,446 | 8/1993 | Dumon . |
| 5,275,622 | 1/1994 | Lazarus . |
| 5,282,824 | 2/1994 | Gianturco . |
| 5,290,305 | 3/1994 | Inone . |
| 5,292,331 | 3/1994 | Boneau . |
| 5,304,200 | 4/1994 | Spaulding . |
| 5,314,472 | 5/1994 | Fontaine . |
| 5,330,500 | 7/1994 | Song ...................................... 606/198 |
| 5,342,387 | 8/1994 | Summers ............................... 606/198 |
| 5,354,309 | 10/1994 | Schnepp-Pesch ........................ 623/12 |
| 5,360,443 | 11/1994 | Barone et al. .......................... 606/195 |
| 5,366,504 | 11/1994 | Anderson et al. . |
| 5,370,683 | 12/1994 | Fontaine . |
| 5,383,928 | 1/1995 | Scott et al. . |
| 5,387,235 | 2/1995 | Chuter . |
| 5,389,106 | 2/1995 | Tower . |
| 5,397,345 | 3/1995 | Lazarus . |
| 5,405,377 | 4/1995 | Cragg . |
| 5,415,664 | 5/1995 | Pinchuk . |
| 5,429,144 | 7/1995 | Wilk . |
| 5,443,496 | 8/1995 | Schwartz . |
| 5,443,498 | 8/1995 | Fontaine . |
| 5,456,713 | 10/1995 | Chuter . |
| 5,464,449 | 11/1995 | Ryan et al. . |
| 5,507,767 | 4/1996 | Maeda . |
| 5,507,771 | 4/1996 | Gianturco . |
| 5,562,724 | 10/1996 | Vorwerk .................................. 623/1 |
| 5,562,727 | 10/1996 | Turk et al. .............................. 623/12 |
| 5,562,728 | 10/1996 | Lazarus et al. ........................ 606/194 |
| 5,571,170 | 11/1996 | Palmaz et al. ......................... 606/108 |
| 5,575,817 | 11/1996 | Martin ..................................... 623/1 |
| 5,662,675 | 9/1997 | Polanskyj-Stockert ..................... 623/1 |
| 5,676,697 | 10/1997 | McDonald ................................ 623/1 |

FOREIGN PATENT DOCUMENTS

| | | |
|---|---|---|
| 0508473 A2 | 10/1992 | European Pat. Off. . |
| 0 540 290 A2 | 5/1993 | European Pat. Off. . |
| 0551179A1 | 7/1993 | European Pat. Off. . |
| 0556850A1 | 8/1993 | European Pat. Off. . |
| 0579523A1 | 1/1994 | European Pat. Off. . |
| 0 536 164 B1 | 3/1994 | European Pat. Off. . |
| 0 481 365 B1 | 6/1994 | European Pat. Off. . |
| 0 621 015 A1 | 10/1994 | European Pat. Off. . |
| 0 621 016 A1 | 10/1994 | European Pat. Off. . |
| 0 622 088 A1 | 11/1994 | European Pat. Off. . |
| 0 646 365 A1 | 4/1995 | European Pat. Off. . |
| 0 656 197 A2 | 6/1995 | European Pat. Off. . |
| 0 657 147 A2 | 6/1995 | European Pat. Off. . |
| 0 662 307 A1 | 7/1995 | European Pat. Off. . |
| 2678508 | 4/1991 | France . |
| 2678508A1 | 1/1993 | France . |
| 3 918 736 A1 | 12/1990 | Germany . |
| 4303181A1 | 8/1994 | Germany . |
| 2106190A | 4/1983 | United Kingdom . |
| WO89/08433 | 9/1989 | WIPO . |
| WO91/07928 | 6/1991 | WIPO . |
| 92/00043 | 1/1992 | WIPO ....................................... 623/1 |
| WO93/13825 | 7/1993 | WIPO . |
| WO94/17754 | 8/1994 | WIPO . |
| WO95/01761 | 1/1995 | WIPO . |

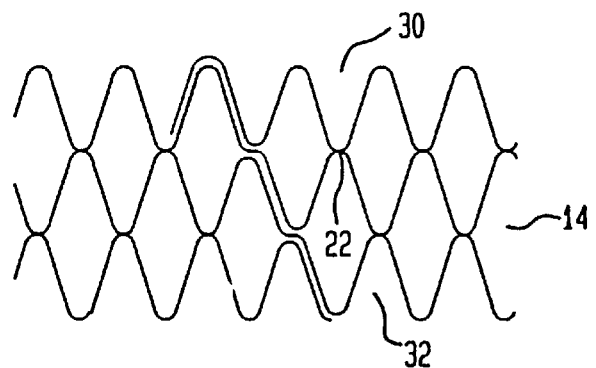
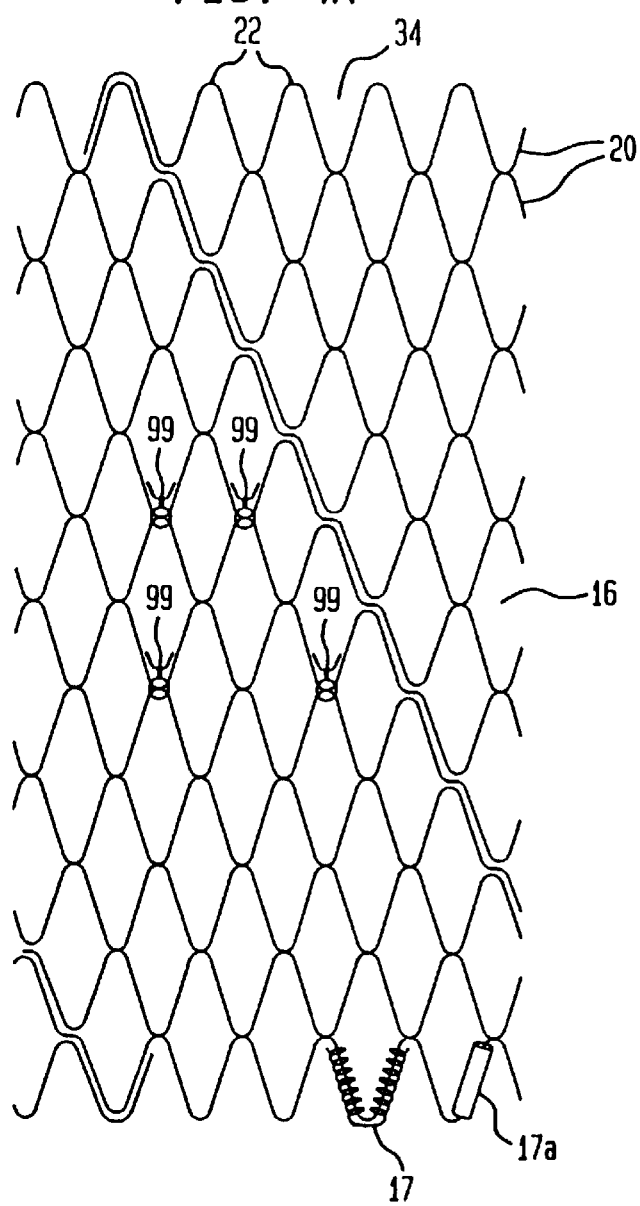

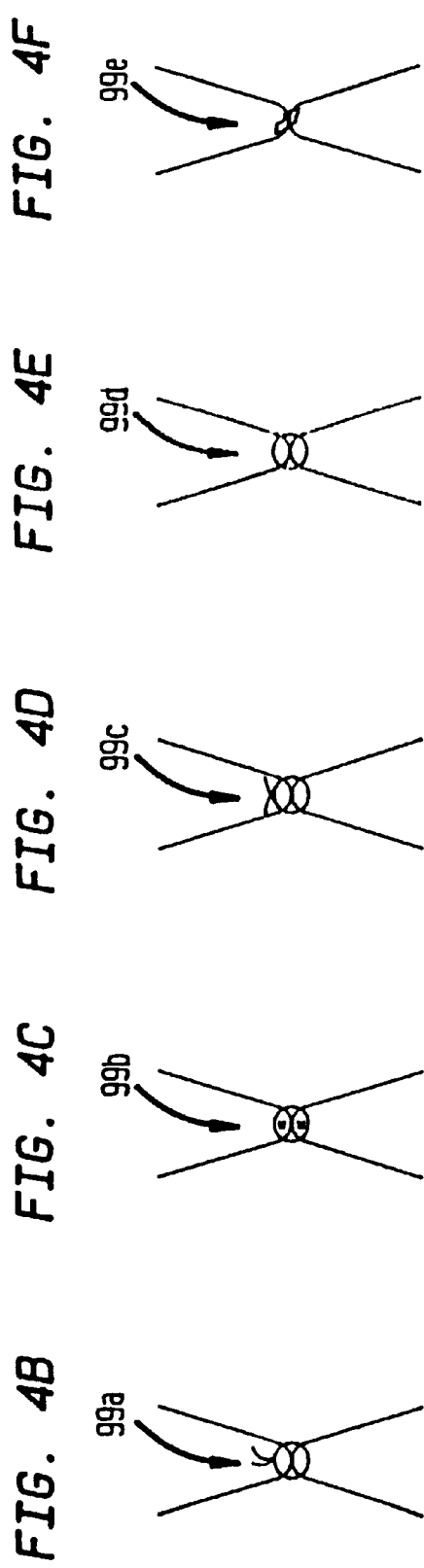

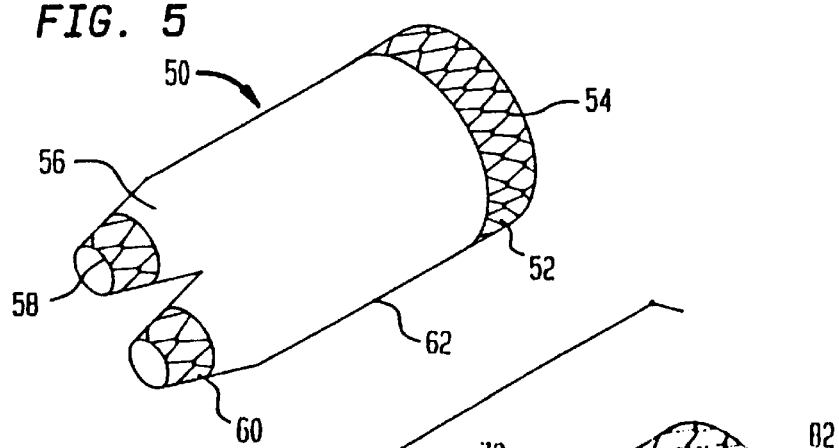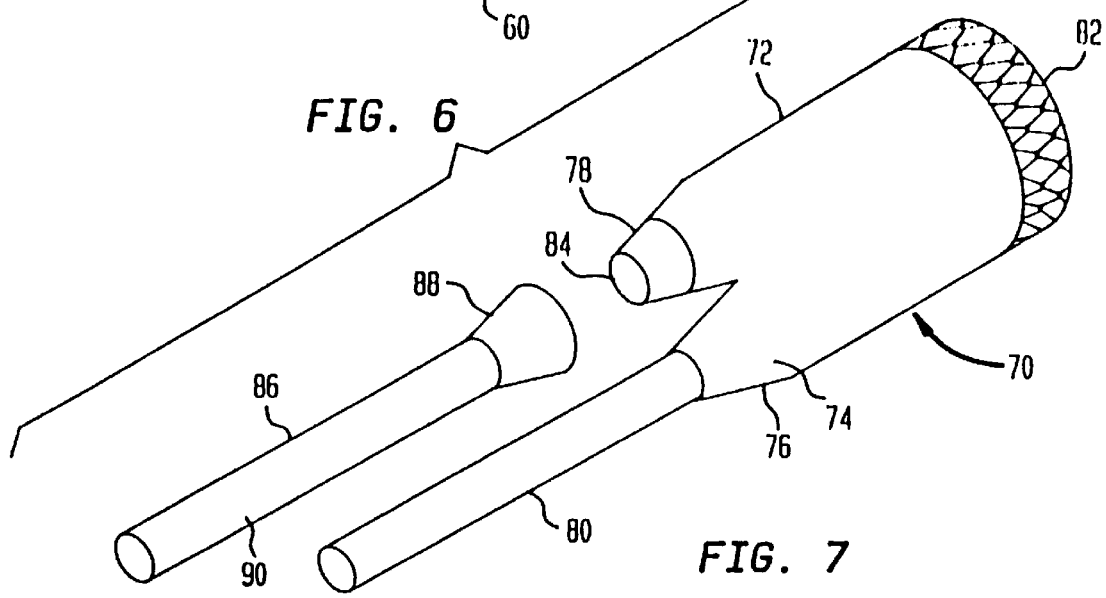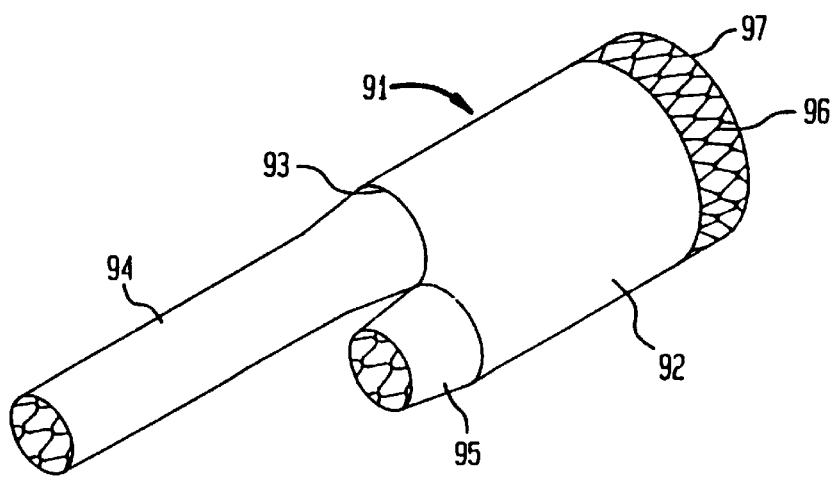

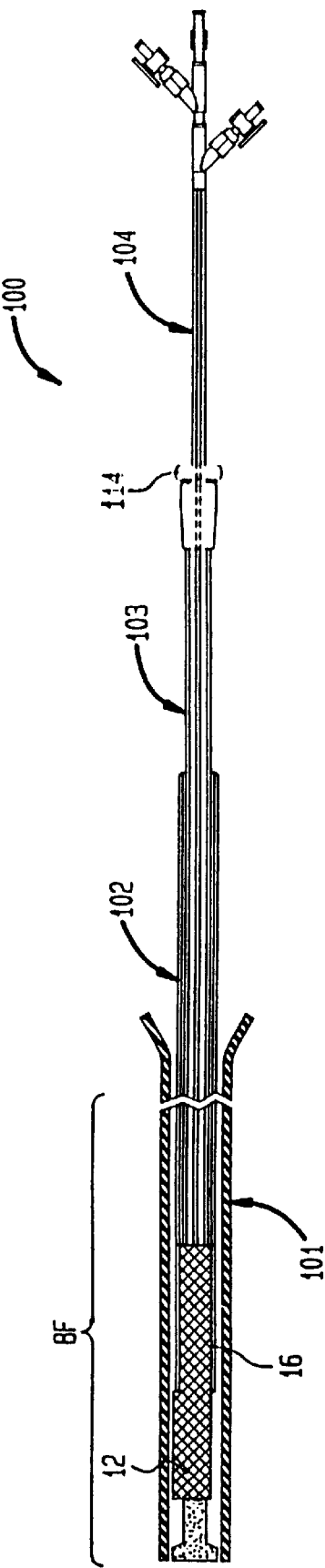

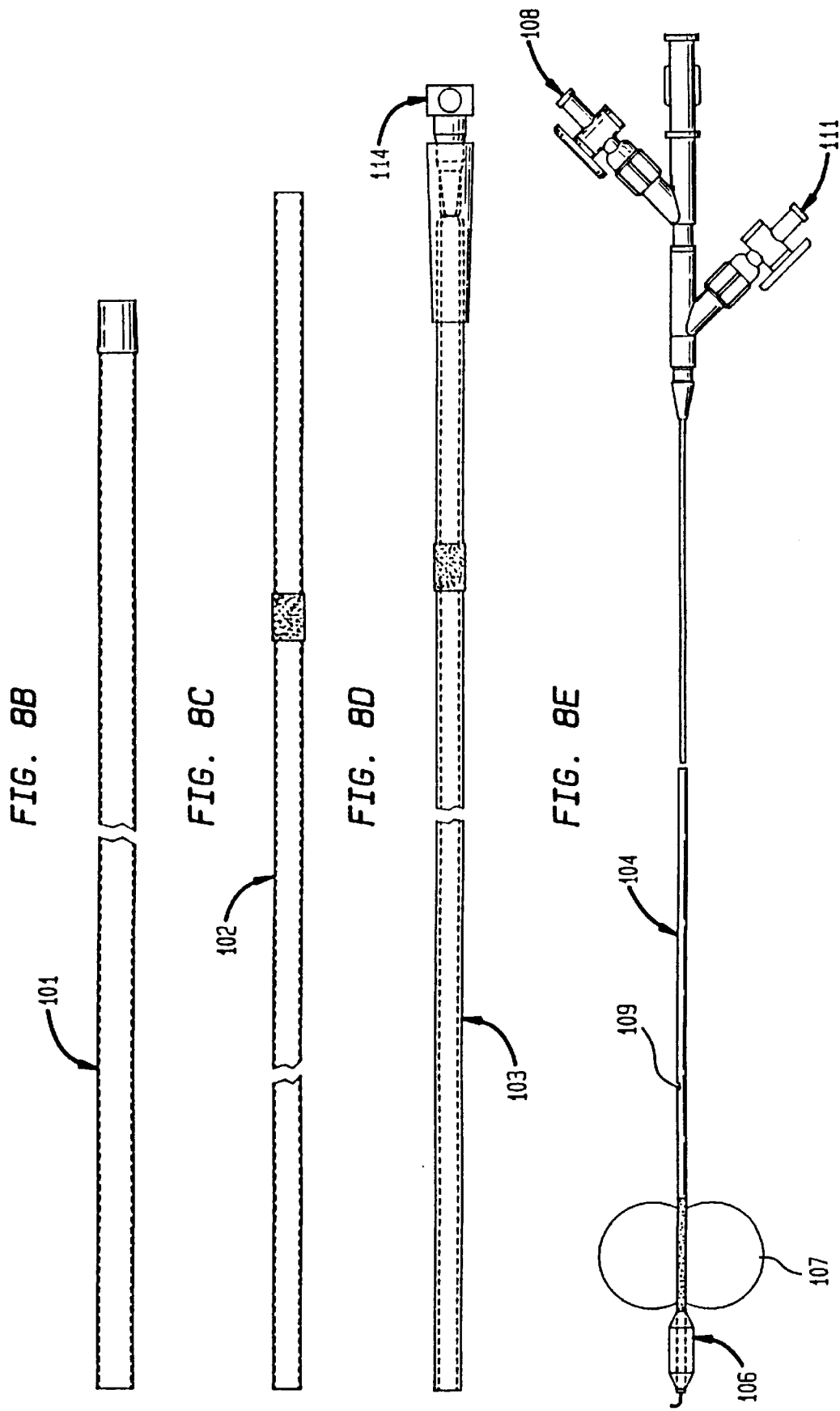

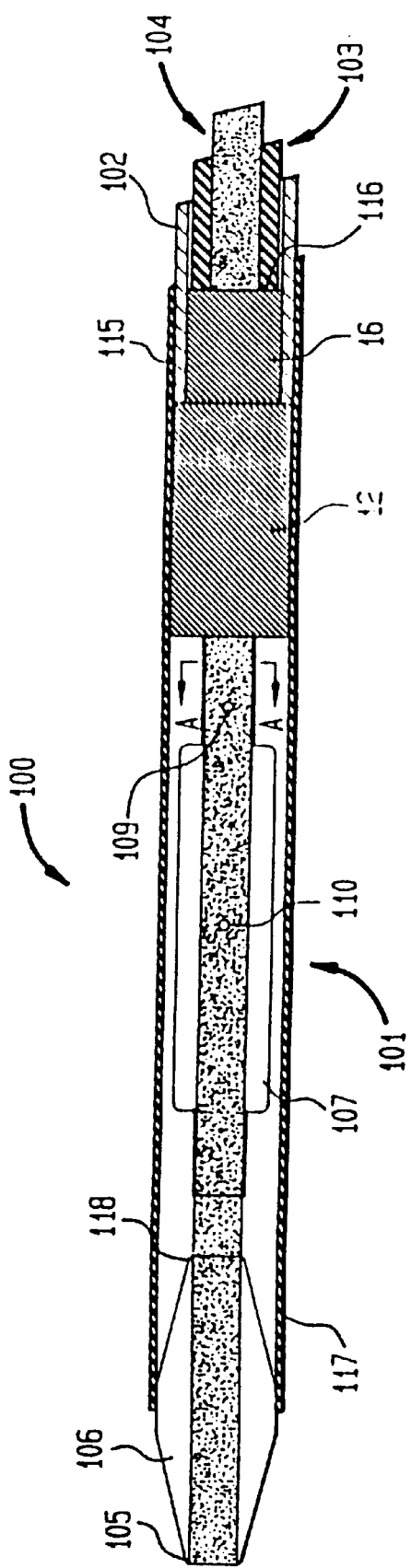

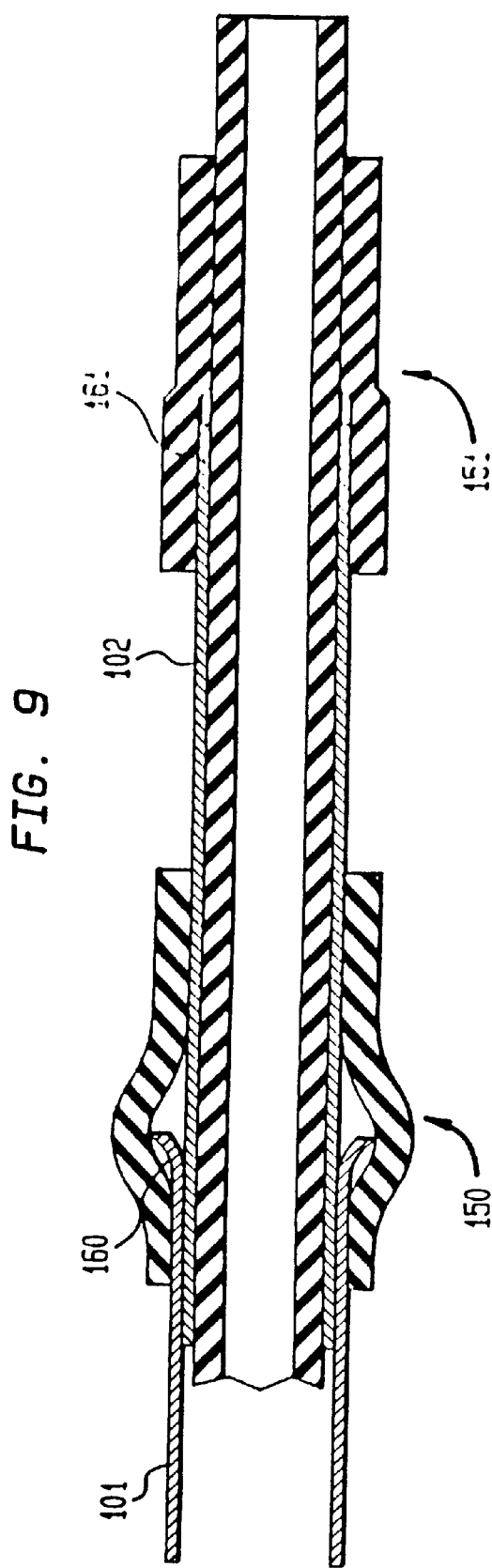

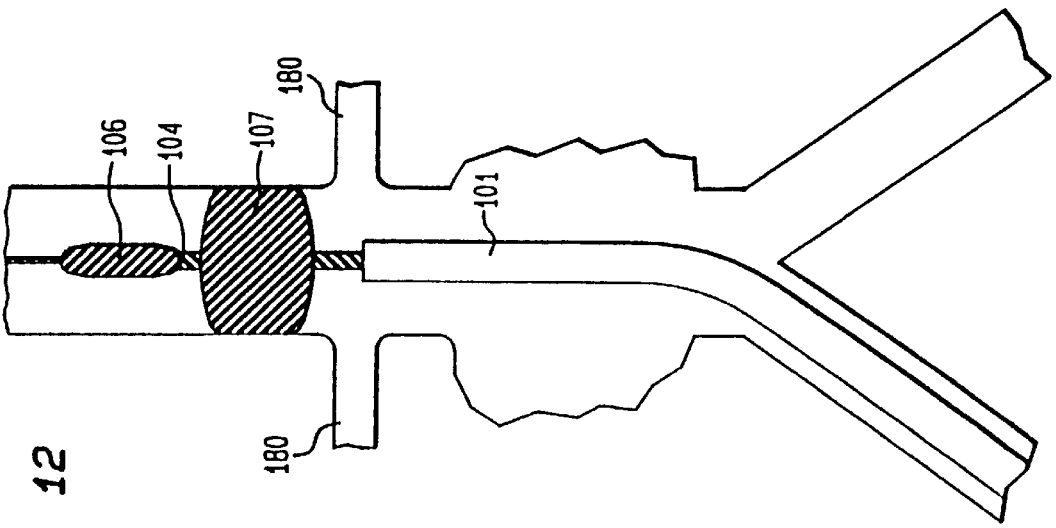
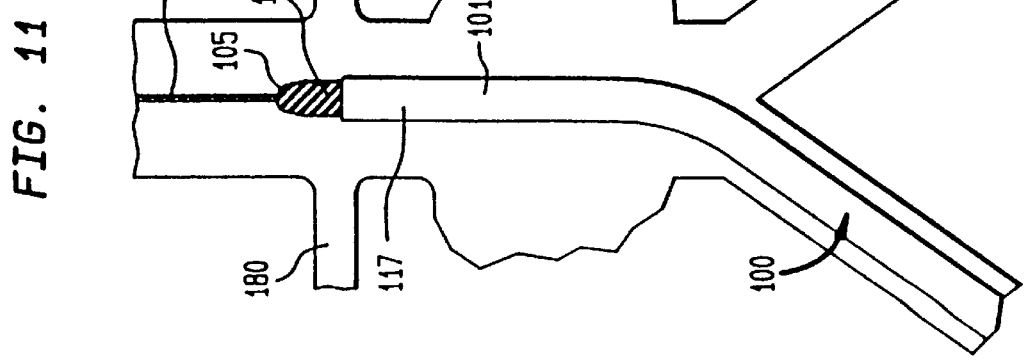

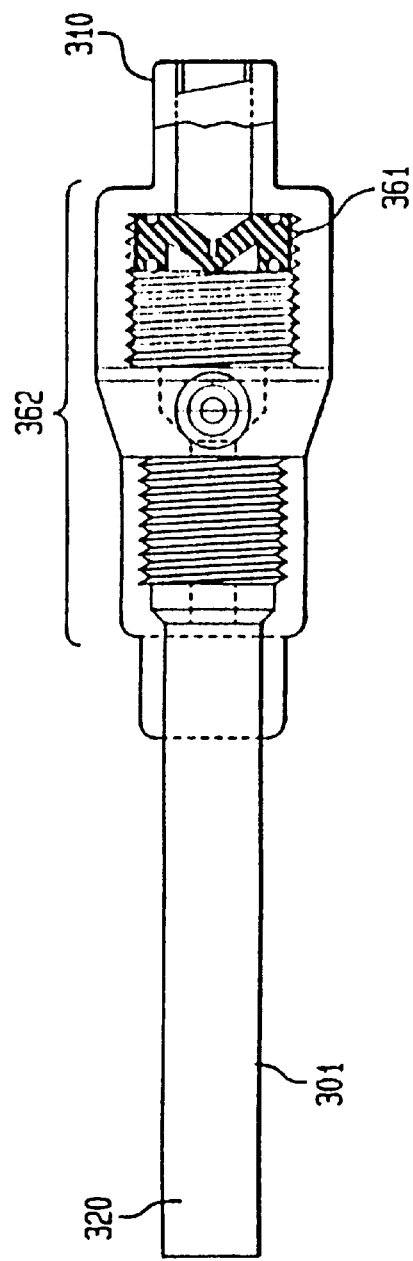
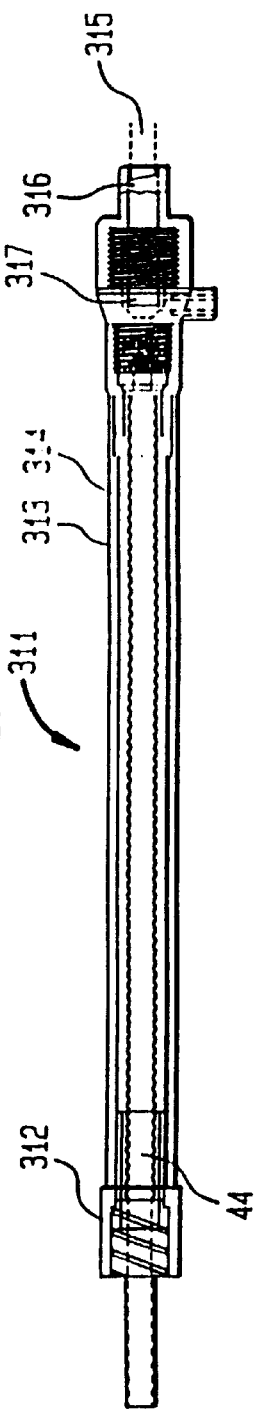
FIG. 21A
FIG. 21B
FIG. 21C

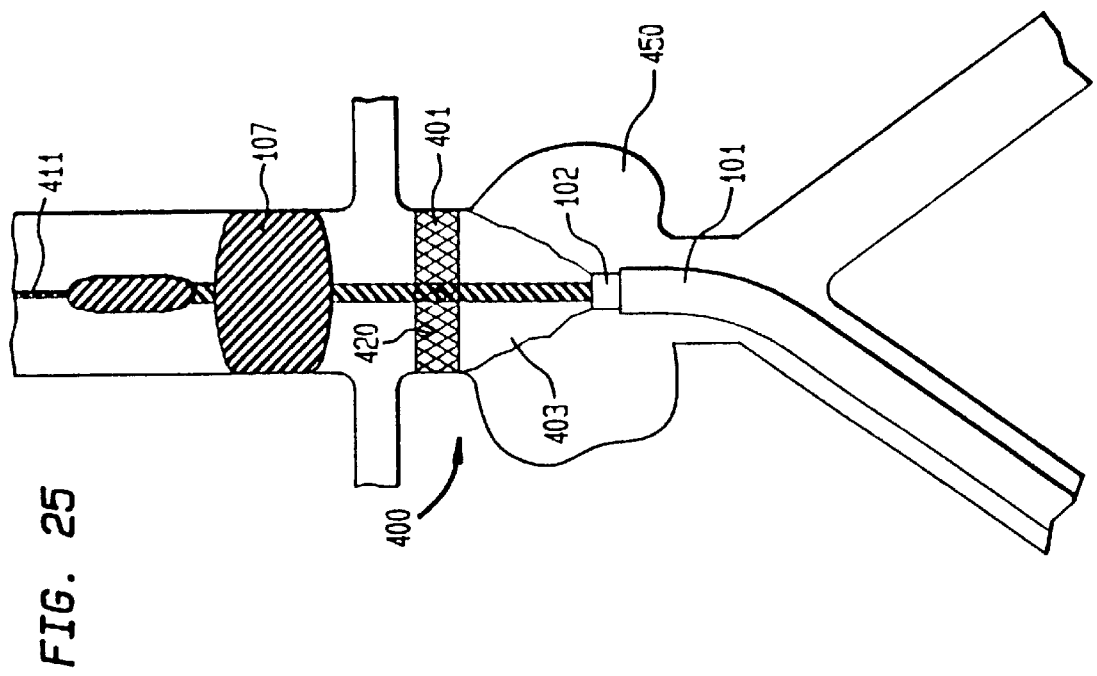

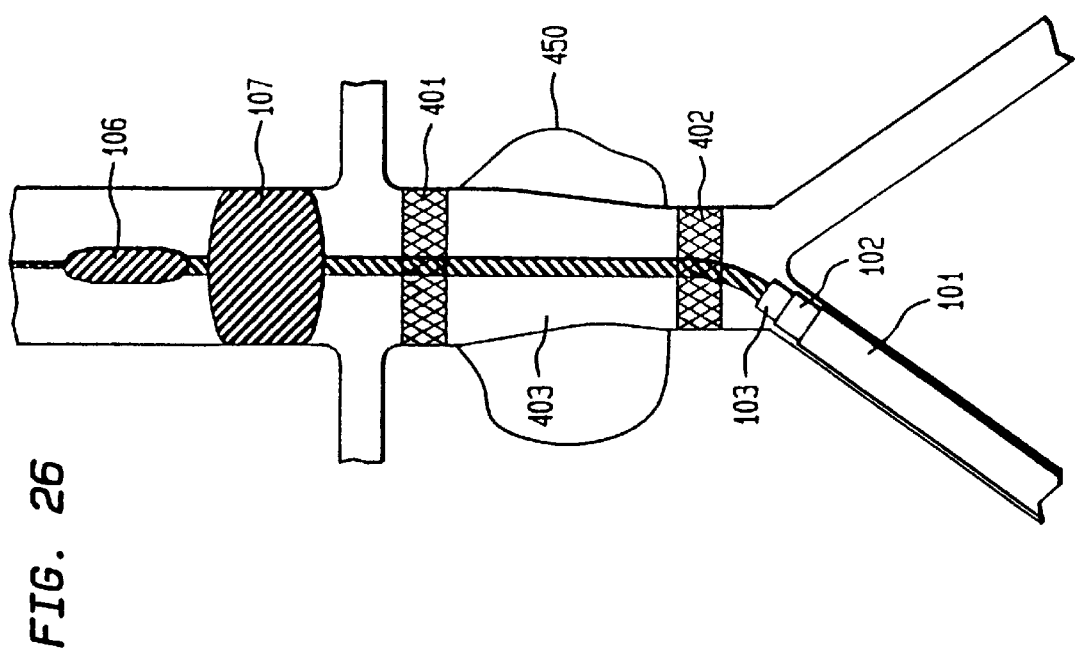

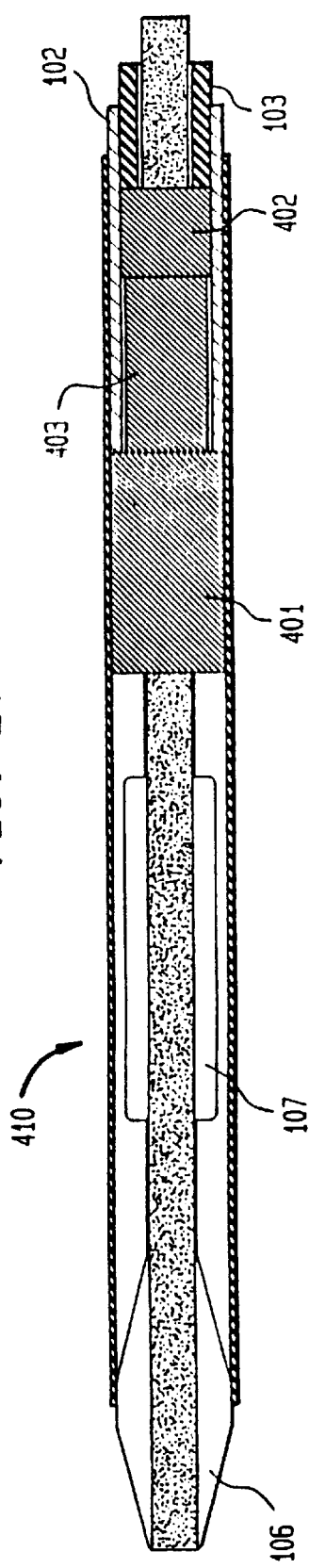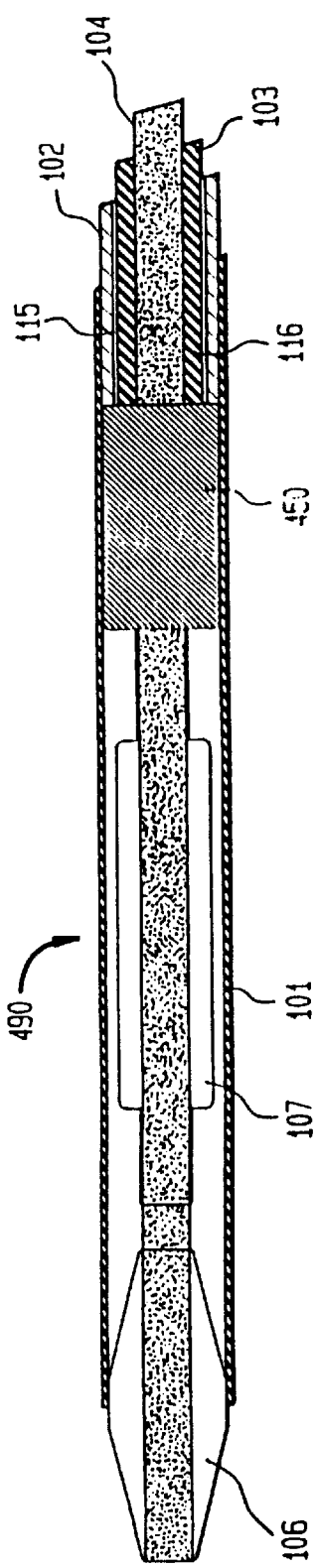

ENDOLUMINAL PROSTHESIS AND SYSTEM FOR JOINING

This is a Continuation of U.S. patent application Ser. No. 08/461,513, filed Jun. 5, 1995 (status: allowed), which is a Divisional of U.S. patent application Ser. No. 08/317,763, filed Oct. 4, 1994 (status: issued), which in turn is a Continuation-In-Part of U.S. patent application Ser. No. 08/312,881, filed Sep. 27, 1994 (status: pending).

This is a continuation-in-part application of the application of common assignment herewith of inventors George Goicoechea, Claude Mialhe, John Hudson and Andrew Cragg, entitled BIFURCATED ENDOLUMINAL PROSTHESIS, filed on Sep. 27, 1994, for which application a serial number had not yet been assigned as of the date of filing this continuation-in-part application.

BACKGROUND OF THE INVENTION

The present invention relates to a bifurcated endoluminal prosthesis for use in a bifurcated blood vessel such, for example, as the infrarenal portion of a mammalian aortic artery where it bifurcates to the common iliac arteries. The present invention also embraces a stent connecting means for connecting a stent (e.g. a stent which forms part of an endoluminal prosthesis) to another stent, as well as apparatus and method for introducing prostheses to the vasculature and methods of treating angeological diseases.

A stent is used to provide a prosthetic intraluminal wall e.g. in the case of a stenosis to provide an unobstructed conduit for blood in the area of the stenosis. An endoluminal prosthesis comprises a stent which carries a prosthetic graft layer of fabric and is used e.g. to treat an aneurysm by removing the pressure on a weakened part of an artery so as to reduce the risk of embolism, or of the natural artery wall bursting. Typically, a stent or endoluminal prosthesis is implanted in a blood vessel at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the catheter is withdrawn and the stent is caused or allowed to re-expand to a predetermined diameter in the vessel.

U.S. Pat. No. 4,886,062 discloses a vascular stent which comprises a length of sinuous or "zig-zag" wire formed into a helix; the helix defines a generally cylindrical wall which, in use, constitutes a prosthetic intraluminal wall. The sinuous configuration of the wire permits radial expansion and compression of the stent; U.S. Pat. No. 4,886,062 discloses that the stent can be delivered percutaneously and expanded in situ using a balloon catheter.

U.S. Pat. No. 4,733,665 discloses an expandable intraluminal graft which is constituted by a tubular member formed from a plurality of intersecting elongate members which permit radial expansion and compression of the stent.

EP-A-0556850 discloses an intraluminal stent which is constituted by a sinuous wire formed into a helix; juxtaposed apices of the wire are secured to one another so that each hoop of the helix is supported by its neighboring hoops to increase the overall strength of the stent and to minimize the risk of plaque herniation; in some embodiments the stent of EP-A-0556850 further comprises a tubular graft member to form an endoluminal prosthesis.

The prior art stents and prostheses mentioned above are generally satisfactory for the treatment of aneurysms, stenoses and other angeological diseases at sites in continuous unbifurcated portions of arteries or veins.

However, the prior art stents and prostheses are not wholly satisfactory for use where the site of desired application of the stent or prosthesis is juxtaposed or extends across a bifurcation in an artery or vein such, for example, as the bifurcation in the mammalian aortic artery into the common iliac arteries. For example, in the case of an abdominal aortic aneurysm ("AAA") in the infrarenal portion of the aorta which extends into one of the common iliac arteries, the use of one of the prior art prosthesis referred to above across the bifurcation into the one iliac artery will result in obstruction of the proximal end of the other common iliac artery; by-pass surgery is therefore required to connect the one iliac artery in juxtaposition with the distal end of the prosthesis to the other blocked iliac artery. It will be appreciated by a person skilled in the art that it is desirable to avoid surgery wherever possible; the requirement for by-pass surgery associated with the use of the prior art prosthesis in juxtaposition with a bifurcation in an artery therefore constitutes a significant disadvantage.

SUMMARY OF THE INVENTION

Throughout this specification, the term "proximal" shall mean "nearest to the heart," and the term "distal" shall mean "furthest from the heart."

According to one aspect of the present invention there is provided a stent connecting means for connecting two intraluminal stents one to the other to define a continuous lumen through the two stents, the stent connecting means including a first stent including a male engaging portion which can be compressed radially inwardly, and a second stent including a female cooperating portion. The male engaging portion may be entered into the female cooperating portion in a radially compressed state and thereafter caused or allowed to expand in the female cooperating portion; the arrangement being such that in service the interengagement of the male engaging portion and the female cooperating portion serves to resist longitudinal separation of the two stents one from the other.

Typically, the first stent may include a proximal male engaging portion; the second stent may include a distal female cooperation portion. The male engaging portion may be flared radially outwardly towards its extremity, and the female cooperating portion may be tapered radially inwardly towards its extremity. In some embodiments, the male engaging portion may comprise a frustoconical wall which flares outwardly towards its longitudinal extremity; the female engaging portion may comprise a frustoconical wall which tapers radially inwardly towards its longitudinal extremity.

Alternatively, said male engaging and female cooperating portions may be substantially untapered; they may be substantially cylindrical.

The male engaging portion of the first stent may be resiliently compressible in a radially inwards direction such that in the radially compressed state it is capable of self-reexpansion to engage in the female cooperating portion. Typically, each of said first and second stents may be resiliently compressible.

In use therefore the second stent may be delivered in a radially compressed state by using a catheter; when the second stent is located at the site of use, the catheter may be withdrawn thereby allowing the second stent to re-expand to engage the endoluminal surface of the blood vessel.

The first stent may then be delivered percutaneously or by a "cut down" technique to a site distal of the second stent such that the male engaging portion of the first stent in the radially compressed state is entered into the expanded female cooperating portion of the second stent; the catheter may then be withdrawn allowing the first stent to re-expand such that the male engaging portion engages in the female cooperating portion of the second stent.

In some embodiments of the present invention the second stent may have two transversely spaced distal female cooperating portions; the second stent may therefore constitute a bifurcated stent for use in juxtaposition with a bifurcation in a blood vessel.

Each of the two transversely spaced distal female cooperating portions may be adapted for connection to a first male stent which, in use, extends across the bifurcation into a respective one of the branched blood vessels.

In a particular aspect of the present invention there is provided a bifurcated intraluminal stent for use in juxtaposition with an angeological bifurcation; the bifurcated intraluminal stent comprising a proximal portion adapted to be positioned in service in a blood vessel in juxtaposition with a bifurcation, a first distal stent portion adapted to extend across the bifurcation into one of the branched blood vessels and a second distal stent portion adapted to allow blood to flow from the proximal portion into the other branched vessel. The first distal stent portion may be formed integrally with the proximal portion.

In some embodiments the second distal stent portion may comprise a female cooperating portion which is adapted to engage a male engaging portion of a another stent adapted to extend in the other branched blood vessel such that, in use, the bifurcated stent can be connected in situ to the other stent. The bifurcated intraluminal stent may therefore constitute a second stent in accordance with the present invention comprising a distal female cooperating portion disposed intermediate the proximal and distal extremities of the stent; the other stent may constitute a first stent in accordance with the present invention.

Typically, the proximal end of said second stent may be flared radially outwardly towards its extremity to engage the endoluminal surface of the artery thereby to resist longitudinal movement of the second stent in service.

Each of the first and second stents may comprise a sinuous wire formed into a tubular configuration. The sinuous and tubular configurations may be imparted to the wire by winding it on a mandrel. Typically, each stent may be made from a shape memory nitinol (nickel-titanium) wire which may be wound on to the mandrel to form the stent in a tubular configuration of slightly greater diameter than the diameter of the blood vessel in which the stent is intended to be used. The stent may be annealed at an elevated temperature and then allowed to cool in air so that the nitinol wire "remembers" the configuration in which it was wound on the mandrel.

Said nitinol wire may be type "M" nitinol wire which is martensitic at temperatures below about 13° C. and is austenitic at temperatures above about 25° C.; it will be appreciated therefore that the type "M" wire will be austenitic at body temperature of 37° C. Typically, the annealing may be conducted at about 500° C. or more for at least about 60 minutes; after cooling the wire may be immersed in cold water to facilitate removal of the wire from the mandrel with the wire in its maleable martensitic form. Typically, the cold water may have temperature of less than about 10° C.; the wire may be immersed for about 5 minutes or more. An advantage of using nitinol wire to form the stent in accordance with the present invention is that the nitinol wire is "super elastic" in its austenitic state; the radial outward force exerted by the stent on the wall of the blood vessel in use is therefore substantially constant irrespective of the diameter of the vessel and the expanded stent.

In some embodiments the wire may have a helical configuration as disclosed in EP-A-0556850. Alternatively, the wire may be of an entirely novel configuration, namely one in which the wire forms a plurality of hoops such that the plane of the circumference of each hoop is substantially perpendicular to the longitudinal axis of the stent. Each hoop may comprise a substantially complete turn of the wire having a sinuous configuration; optionally, as each hoop is completed, the point of winding the wire may be displaced longitudinally with respect to the winding axis to form the next hoop. When the next hoop is complete, the point of winding is moved further longitudinally with respect to the winding axis to the form the next succeeding hoop and so on.

It will appreciated that an advantage of this novel arrangement is that the planes of the hoops are not skewed with respect to the longitudinal axis of the stent; the longitudinal ends of the stent are "square" to said longitudinal axis, so that when the stent is caused or allowed to expand in situ there is substantially no twisting of the stent as it shortens in length. It will be appreciated that this represents a significant advantage, as in areas of stenosis or aneurysm it is desirable to minimize the movement of the stent within the blood vessel so as to reduce the potential trauma to the patient. A stent of this configuration may be used, apart from the bifurcated embodiment otherwise taught herein, in any application which in stents generally have heretofore been used.

Typically, the stents of this invention whether of the helical or perpendicular variety, also comprise a securing means for securing an apex of the sinuous wire in one hoop to a juxtaposed apex of a neighboring hoop so that each hoop is supported by its neighbors. The securing means may comprise a loop element of a suture material, for example, to tie the juxtaposed apices together; the loop element may also comprise a loop formed of a thermoplastics material such, for example, as polypropylene. Alternatively, the securing means may be a bead formed of a thermoplastic material around juxtaposed apices. Also alternatively, the securing means may be a loop, ring, or staple formed of wire such as nitinol.

The male engaging portion and female cooperating portion, of the first and second interengaging stents of this invention, may be formed separately from the remainder of the respective non-engaging portions of these stents and then the engaging and non-engaging portions secured to one another by securing means.

In one embodiment of the present invention, the proximal and distal stent portions of the bifurcated stent in accordance with the present invention may be formed separately; the distal end of the proximal stent portion may be secured to the wider proximal end of a first intermediate frustoconical stent portion; the narrower distal end of the first intermediate frustoconical stent portion may be secured to the proximal end of the distal stent portion. The female cooperating portion of the bifurcated stent may be constituted by a second frustoconical stent portion which is secured to the distal end of the proximal stent portion in juxtaposition with the first frustoconical portion.

Alternatively the first and second frustoconical portions may be omitted; the proximal and distal stent portions may be secured directly one to the other.

The female cooperating portion may be constituted by a generally cylindrical stent portion secured to said proximal stent portion in transversely spaced relation to the distal portion.

Each of the first and second stents of the bifurcated form of the present invention may carry a tubular graft layer formed from a biocompatible fabric in juxtaposition with the stent; the combined stent and graft layer constituting an endoluminal prosthesis. Typically the graft layer may be disposed externally of the stent; it will be appreciated however that in some embodiments the graft layer may be disposed internally of the stent. In some embodiments the graft layer may be secured to the stent by loop elements such, for example, as loops of polypropylene. The biocompatible fabric may be a polyester fabric or a polytetrafluoroethylene fabric; typically said fabric may be woven or a warp knitted polyester fabric. In some embodiments the woven or a warp knitted fabric may be formed in a seam-free bifurcated configuration as a sleeve for a bifurcated stent.

In some embodiments the male engaging portion of the first stent and the female cooperating portion of the second stent may be left uncovered. Alternatively, the fabric graft layer may extend to the proximal extremity on the external surface of the male engaging portion, and may be folded over the distal extremity of the female engaging portion to form an inner sleeve; in use the external fabric of the male engaging portion may butt against the folded over portion of the fabric internally of the female cooperating portion to form a substantially blood tight seal.

The present invention in one aspect therefore includes a bifurcated endoluminal prosthesis comprising a bifurcated stent in accordance with the invention and a tubular graft layer.

The first stent having the male engaging portion may also have a tubular graft layer. If required the first prosthesis may be introduced in a radially compressed state such that the male engaging portion of the first prosthesis is engaged in the intermediate female cooperating portion of the bifurcated prosthesis; the first prosthesis is then caused to be allowed to re-expand in situ such that the male engaging portion engages in the female cooperating portion to resist longitudinal separation of the two prosthesis in service.

The bifurcated prosthesis may be adapted for use in the infrarenal portion of a mammalian aorta in juxtaposition with the bifurcation of the common iliac arteries for the treatment of abdominal aortic aneurysms. In use the bifurcated endoluminal prosthesis may be introduced into the infrarenal portion of the aorta using a catheter such that the first distal stent portion extends into one of the branched iliac arteries; the catheter may then be withdrawn allowing the prosthesis to re-expand in situ.

It will be appreciated by a person skilled in the art that the prostheses may be introduced to the site of use percutaneously or by "cut down" techniques.

Any of the stents according to this invention may be provided on its external surface with circumferentially spaced wire barbs or hooks adapted to engage in the endoluminal surface of the host artery to resist longitudinal movement or slippage of the stent in use. Typically the barbs or hooks may be disposed on part of the stent which is provided with a fabric graft layer such that in use the points of the artery which are engaged by the barbs or hooks are covered by the fabric graft. It will be appreciated by a person skilled in the art that the trauma to the artery wall caused by the hooks or barbs may cause emboli; the provision of the fabric graft over the barbs or hooks in use will therefore help to prevent the introduction of such emboli into the blood stream.

The male engaging portion for the first stent may be provided with circumferentially spaced hooks or barbs on its external surface to engage the internal surface of said female cooperating means, thereby to reinforce the connecting means against longitudinal separation of the stents one from the other in the service.

The present invention therefore provides a connecting means for connecting two stents longitudinally one to the other. It will be appreciated that this represents a significant step forward in the art as it allows the provision of a bifurcated endoluminal prosthesis for use in juxtaposition e.g. with arterial bifurcations without requiring by-pass surgery to connect one of the branched arteries to the other branched artery.

In particular, the invention provides a bifurcated endoluminal prosthesis which can be positioned in an artery in juxtaposition with a bifurcation to extend into one of the branched arteries; the bifurcated prosthesis can be connected to another prosthesis which extends into the other branched artery. The prosthesis can be delivered percutaneously or by "cut down" methods and connected together in situ thereby to provide effective treatment of an angeological disease such, for example, as an aneurysm or a stenosis which extends across a bifurcation in a blood vessel without the need for by-pass surgery.

In another aspect, this invention provides an introducer for delivering, into the vasculature at an angeological bifurcation where a blood vessel branches into two branched vessels, a bifurcated endoluminal stent or prosthesis having a proximal portion adapted to be disposed in the blood vessel and a distal portion adapted to be disposed at least partially in one of the two branched vessels. The introducer comprises a tubular outer sheath, a proximal portion pusher disposed at least partially within the outer sheath, and a distal portion pusher disposed at least partially within the proximal portion pusher.

The present invention further provides an introducer for delivering into the vasculature at an angeological bifurcation where a blood vessel branches into two branched vessels, an endoluminal prosthesis having a proximal stent portion and a distal stent portion. The introducer comprises a tubular outer sheath, a proximal portion pusher disposed at least partially within the outer sheath and having a proximal end adapted to contact the proximal stent portion, a distal portion pusher disposed at least partially within the proximal portion pusher and having a proximal end adapted to contact the distal stent portion; and a balloon catheter, having a balloon attached thereto, disposed at least partially within the distal portion pusher.

This invention in another aspect provides a method for delivering a bifurcated endoluminal stent or prosthesis having a proximal portion and a first distal portion into the vasculature at an angeological bifurcation where a blood vessel branches into a first branched vessel and a second branched vessel. The method comprises inserting a first introducer containing the stent or prosthesis into the vasculature to a predetermined delivery location, the first introducer comprising an outer sheath, a proximal portion pusher, and a distal portion pusher; withdrawing the outer sheath of the first introducer while maintaining the proximal portion pusher in a fixed position until the proximal portion of the stent or prosthesis is deployed from the first introducer into the blood vessel; withdrawing the outer sheath and the proximal portion pusher while maintaining the distal portion pusher in a fixed position until the first distal portion of the stent or prosthesis is deployed from the first introducer at least partially into the first branched vessel; and withdrawing the first introducer from the vasculature.

This invention further provides a method for delivering, into the vasculature at an angeological bifurcation where a blood vessel branches into two branched vessels, an endoluminal prosthesis having a proximal stent portion, and a distal stent portion. The method comprises the steps of inserting an introducer containing the prosthesis into the vasculature to a predetermined delivery location, the introducer comprising an outer sheath, a proximal stent portion pusher, a distal stent portion pusher, and a balloon catheter having a balloon attached thereto; inflating the balloon to at least partially block blood flow in the blood vessel; withdrawing the outer sheath of the introducer while maintaining the proximal stent portion pusher in a fixed position until the proximal stent portion of the prosthesis is deployed from the introducer into the blood vessel; withdrawing the outer sheath and the proximal stent portion pusher while maintaining the distal stent portion pusher in a fixed position until the distal stent portion of the prosthesis is deployed from the introducer into the blood vessel; and withdrawing the introducer from the vasculature.

In general, this invention provides a method of treating an angeological disease at a bifurcation site where a blood vessel branches into a first branched vessel and a second branched vessel comprising the steps of disposing in the blood vessel a proximal portion of an endoluminal stent; directing blood flow from the blood vessel into the first branched vessel through a first distal portion of the endoluminal stent, the first distal portion being connected to the proximal portion and extending into the first branched vessel; and directing blood flow from the blood vessel into the second branched vessel through a second distal portion of the endoluminal stent, the second distal portion being connected to the proximal portion and extending into the second branched vessel. This method may be applied to aneurysms, occlusions, or stenosis.

Following is a description by way of example only and with reference to the accompanying drawings of the present invention, including novel stent constructions and methods of manufacture and use thereof.

BRIEF DESCRIPTION OF THE DRAWINGS

The aspects, features and advantages of the present invention will be more readily understood from the following detailed description when read in conjunction with the accompanying drawings, in which:

FIG. 1b is a front view of another stent which is adapted to be connected to the bifurcated stent of FIG. 1a.

FIG. 3 is a side view of another part of the bifurcated stent of FIG. 1a opened up to show its construction.

FIG. 4(a) is a side view of yet another part of the bifurcated stent of FIG. 1a opened up to show its construction.

FIGS. 4(b)–4(f) are partial exploded views of the exemplary stent of FIG. 4(a) illustrating alternative means for securing juxtaposed apices according to the present invention.

FIG. 5 is a schematic perspective view of a bifurcated endoluminal prosthesis in accordance with the present invention.

FIG. 6 is a schematic view of another bifurcated endoluminal prosthesis in accordance with the present invention.

FIG. 7 is a schematic view of yet another bifurcated endoluminal prosthesis in accordance with the present invention.

FIG. 8(a) is a cross-sectional view of an exemplary assembled introducer according to the present invention.

FIGS. 8(b)–8(e) are side views of the component parts of the introducer of FIG. 8(a).

FIG. 8(f) is a partial cross-sectional view of the introducer of FIG. 8(a).

FIG. 8(g) is a cross-sectional view of part of the introducer of FIG. 8(f) taken along the line A—A.

FIG. 9 is a side cross-sectional view of a portion an alternative embodiment of an introducer according to the present invention.

FIGS. 11 through 20 are sequential cross-sectional views of the bifurcation of the abdominal aortic artery during introduction of an exemplary prosthesis according to the present invention.

FIGS. 21(a)–21(c) are cross-sectional views is of alternative insertion apparatus according to the present invention.

FIGS. 24(a), 24(b), 25, 26 and 27 are sequential cross-sectional views of the bifurcation of the abdominal aortic artery during introduction of an exemplary prosthesis according to the present invention.

FIGS. 28 and 29 are cross-sectional side views of alternative delivery apparatus according to the present invention.

DETAILED DESCRIPTION

Parent application Ser. No. 08/461,513, filed, Jun. 5, 1995 is incorporated by reference herein, in its entirety.

The present invention includes apparatus and method for treating angeological diseases in any bifurcated blood vessel. One example of such a bifurcated blood vessel is the infrarenal portion of a mammalian aortic artery where it bifurcates to the common iliac arteries. Examples of diseases that can be treated using the apparatus and method of the present invention include aneurysm, stenosis, and occlusion.

Figure 1A:
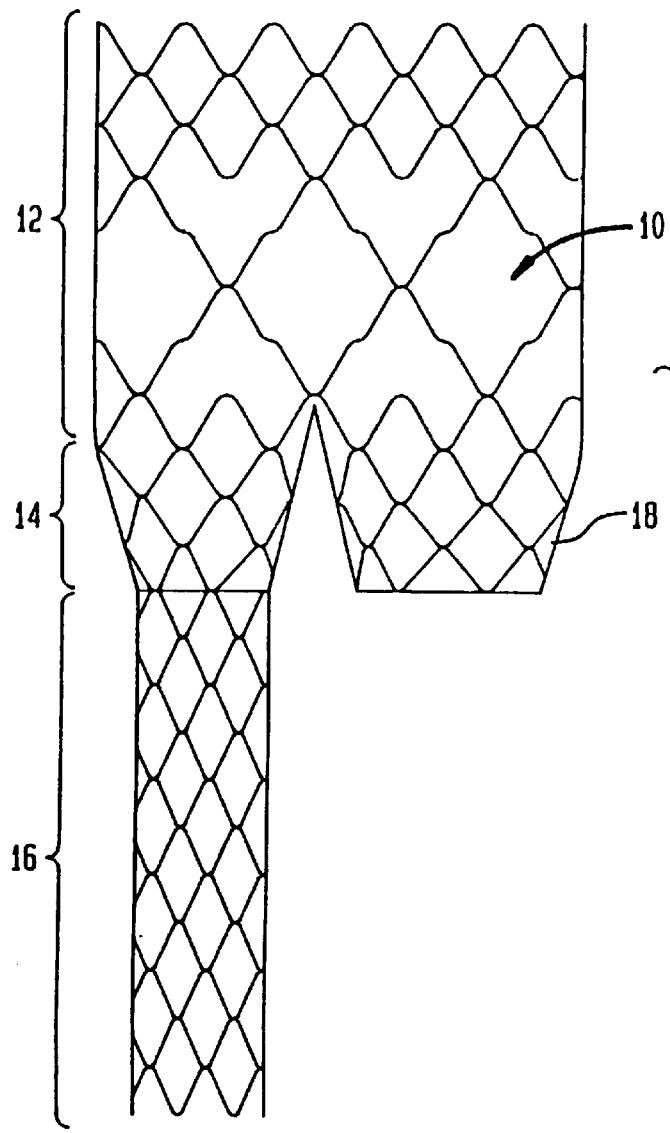
FIG. 1a is a front view of a bifurcated intraluminal stent in accordance with the present invention constituting part of an endoluminal prosthesis.

A bifurcated stent in accordance with the present invention which is indicated at 10 in FIG. 1a comprises a wire skeleton which is constructed in four separate parts, namely a proximal part 12, a first frustoconical part 14, a first distal part 16 and a second frustoconical part 18. Said bifurcated stent 10 carries a fabric graft layer (FIGS. 5, 6, and 7) for use as an endoluminal prosthesis e.g. in the infrarenal portion of a mammalian aorta in juxtaposition with the bifurcation of the common iliac arteries. It will be appreciated, however, that bifurcated stents (with or without fabric graft layers) for use in different parts of the angeological system and for different mammals can be constructed in accordance with the invention by varying the dimensions of the stent accordingly.

Each of the four parts of the bifurcated stent 10 is made in substantially the same way by winding a shape memory nitinol wire, typically nitinol type M wire, onto a mandrel 46.

Figure 2A:
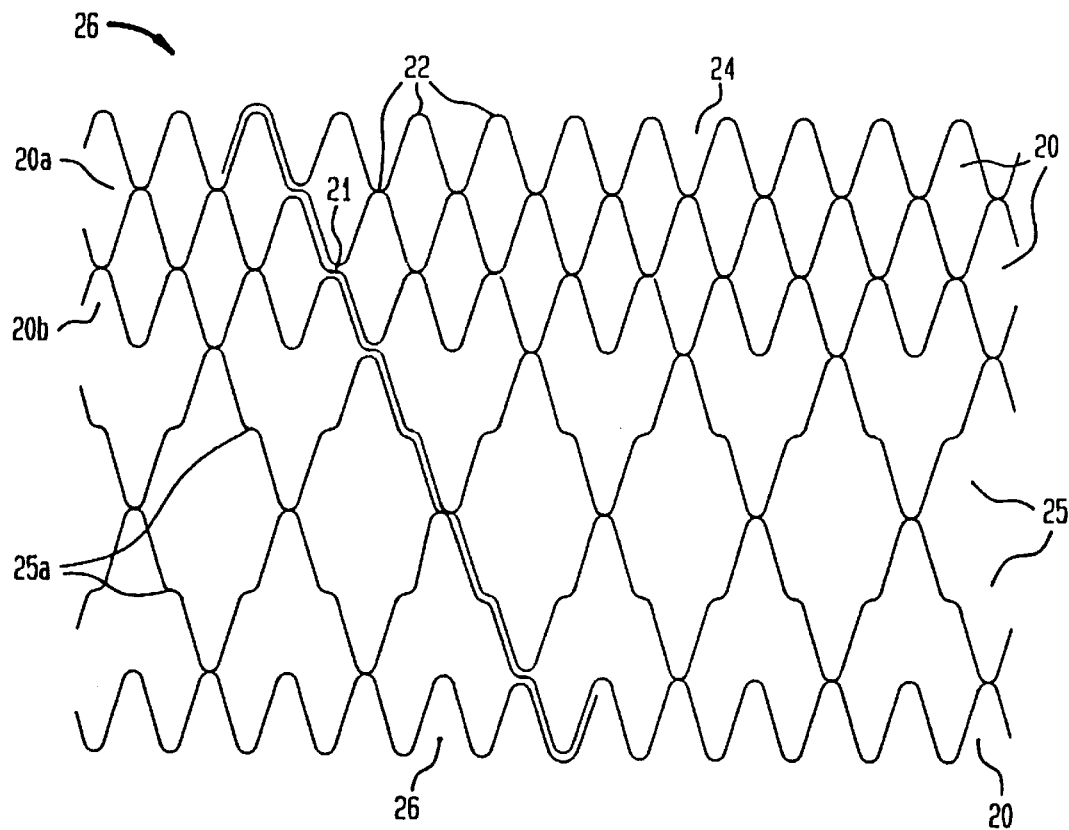
FIG. 2(a) is a side view of part of the bifurcated stent of FIG. 1a opened up to show its construction.
Figure 2B:
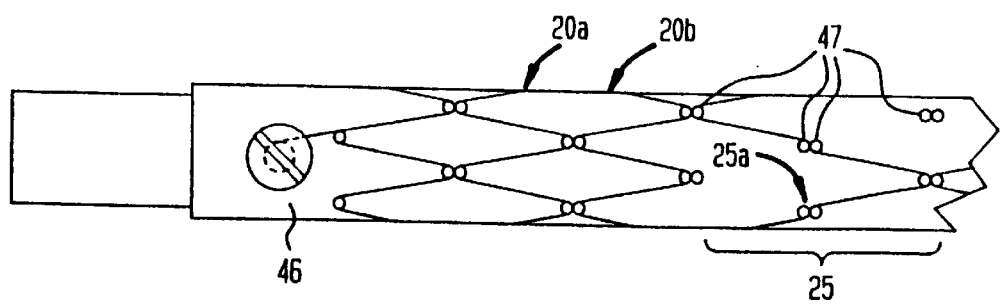
FIG. 2(b) is a side view of an exemplary mandrel used to form the part of the bifurcated stent shown in FIG. 2(a).

The construction of the exemplary proximal part 12 of the bifurcated stent 10 is shown in FIGS. 2(*a*) and 2(*b*); nitinol wire type M wire typically having a diameter of 0.46 mm (0.018") is wound around mandrel 46 to form a plurality of hoops 20. The winding surface of mandrel 46 is provided with a plurality of upstanding pins 47 disposed in a zig-zag pattern for each of the hoops 20 so that in each hoop 20 the nitinol wire follows a sinuous path to define a plurality of circumferentially spaced apices 22. Each hoop 20 is wound onto mandrel 46 such that the plane of the circumference of each hoop 20 is substantially perpendicular to the longitudinal axis of the mandrel.

When one hoop 20 e.g. the hoop indicated at 20*a* has been formed, the point of winding of the nitinol wire is displaced longitudinally with respect to the axis of mandrel 46 to form the next successive hoop 20*b*. The stent shown in FIG. 2(*a*) is the stent formed on mandrel 46 shown in FIG. 2(*b*) after cutting the stent longitudinally and rotating it 45 degrees to show the construction of the stent.

The proximal part of the exemplary bifurcated stent of FIG. 1*a* is formed on the mandrel with a diameter of about 24 mm and a length in the longitudinal direction of about 55 mm. From FIGS. 1(*a*), 2(*a*), and 2(*b*) it will be noted that the proximal part 12 is constituted by three hoops 20 of unit width at the proximal end 24 of the proximal part 12, two intermediate hoops 25 of twice unit width and, at its distal end 26, by a single hoop 20 of unit width. In the illustrated embodiment, intermediate hoops 25 have a plurality of offsets 25*a*. Offsets 25*a* are formed when the wire is passed around pins 47 on mandrel 46. Offsets 25*a* add stability to the stent. When the nitinol wire has been wound onto mandrel 46, the nitinol wire is annealed at an elevated temperature and then allowed to cool.

In this embodiment of the invention the wire is annealed at a temperature of about 500° C. for 60 minutes and is then allowed to cool in air. The purpose of the annealing is so that the nitinol wire in its austenitic form "remembers" its configuration as wound on mandrel 46; it will be appreciated therefore that other temperatures and durations for the annealing are included within the present invention provided the nitinol wire "remembers" its wound configuration.

After annealing and cooling, the wire is immersed in cold water at less than 10° C. for about 5 minutes; the wire is then removed from the mandrel, and juxtaposed apices 22 of neighboring hoops 20 are secured together by securing means 99 (see FIG. 4(*a*)), which are, in this example, 0.003" polypropylene filaments. Each apex 22 of each hoop 20 which has a juxtaposed apex of a neighboring hoop 20 is tied to the juxtaposed apex 22. It will be appreciated, however, that in other embodiments of the invention only some of the juxtaposed apices 22 may be secured in this way.

In addition to polypropylene filaments, the securing means may comprise a loop element 99*a* of a suture material, for example, to tie the juxtaposed apices together, as shown in FIG. 4(*b*). The securing means may also comprise bead 99*b* formed of a thermoplastic material around juxtaposed apices, as shown in FIG. 4(*c*). Also alternatively, the securing means may be a loop 99*c*, ring 99*d*, or staple 99*e* formed of wire such as nitinol, as shown in FIGS. 4(*d*), 4(*e*), and 4(*f*) respectively.

The exemplary first and second frustoconical parts 14, 18 of the skeleton shown in the figures are formed in substantially the same way as the proximal part 12 by winding nitinol wire onto a mandrel and then annealing the wire before removing it from the mandrel. As shown in FIG. 3, the first and second frustoconical parts 14, 18 are each constituted by three hoops 20 of unit width. The mandrel is tapered such that the proximal end of each of the exemplary frustoconical parts 14, 1*a* is formed with a diameter of about 12 mm and the distal end 32 of each is formed with a diameter of about 9 mm. The overall length of each of the exemplary frustoconical parts 14, 18 is about 18 mm. The wire used for the frustoconical parts 14, 18 is nitinol type M wire having a diameter of 0.28 mm (0.011"). Juxtaposed apices 22 of each of the exemplary frustoconical parts 14, 18 are tied together using 0.03" polypropylene filaments as described above. The first and second frustoconical parts 14, 18 are secured to the distal end 26 of the proximal part 12 of the stent 10 in transversely spaced relation as shown in FIG. 1*a* by securing the apices 22 of the hoop 20 forming the wider proximal end 30 of each of the frustoconical parts 14, 18 to juxtaposed apices 22 of the hoop 20 on the distal end 26 of the proximal part 12.

The exemplary first distal part 16 of the bifurcated stent 10 is formed by winding nitinol type M wire typically having a diameter of 0.28 mm (0.011") onto a mandrel to form twelve longitudinally spaced hoops 20 as shown in FIG. 4; the exemplary first distal part has an overall length of about 66 mm and a uniform diameter of about 9 mm. The proximal end 34 of the distal part 16 is secured to the narrower distal end 32 of the first frustoconical part 14 by tying each apex 22 on the proximal end 34 of the first distal part 16 to a juxtaposed apex on the distal end 32 of the first frustoconical part 14 using, in this embodiment, 0.003" polypropylene filaments.

The proximal part 12, the first and second frustoconical parts 14, 18, and the first distal part 16 are each covered with a tubular graft layer of a biocompatible woven fabric (FIGS. 5, 6, and 7) such, for example, as a plain woven fabric made from 30 or 40 denier polyester. The tubular fabric layers may be attached to the proximal and distal parts 12, 16 of the stent 10 by stitching with, for example, 0.003" polypropylene filaments around the apices 22 of the underlying skeleton. The fabric covered stent constitutes one form of an endoluminal prosthesis.

The proximal part 12 of the wire skeleton may be provided with a plurality of circumferentially spaced hooks or barbs 43 which project through the tubular fabric layer to engage in the endoluminal surface of a host artery in service.

The sinuous configuration of each turn 20 of the wire skeleton of the stent 10 allows the prosthesis to be compressed resiliently radially inwards so that it can be received in a catheter e.g. a 16 or 18 French catheter for percutaneous or cut down delivery, e.g. to an intraluminal site in the infrarenal section of the aortic artery. Larger diameter catheters up to, e.g., 20 French, may be used to deliver the prosthesis using "cut down" procedures.

An x-ray opaque marker may be attached to one or more ends of a stent so that the delivery of the stent can be monitored using x-rays. As shown in FIG. 4(*a*), such a radiopaque marker may typically comprise a gold or platinum wire 17 crimped onto an end of stent 16. Alternatively, the radiopaque marker may be a tube 17*a* disposed around a length of wire on the stent, also as shown in FIG. 4(*a*). Typically, in the bifurcated stent the marker is secured to the stent in line with the distal stent portion so that the distal stent portion can be aligned with and inserted into one of the branched arteries in situ.

The bifurcated endoprosthesis is positioned in the infrarenal section of the aortic artery in juxtaposition with the bifurcation of the common iliac arteries such that the first distal part 16 of the prosthesis extends into one of the common iliac arteries. The catheter is then withdrawn allowing the stent 10 to re-expand towards its configuration as wound on the mandrel in which it was annealed until the stent engages the endoluminal surface of the host artery. The barbs or hooks engage the endoluminal surface of the host artery to resist longitudinal displacement or slipping of the prosthesis in use.

It will be appreciated that when the bifurcated prosthesis is positioned and re-expanded in the fitted position, blood can flow from the aortic artery into the proximal part 12 of the prosthesis from where it can flow into the one common iliac artery through the frustoconical part 14 and the first distal part 16 and also into the other common iliac artery through the second frustoconical part 18.

Figure 1B:
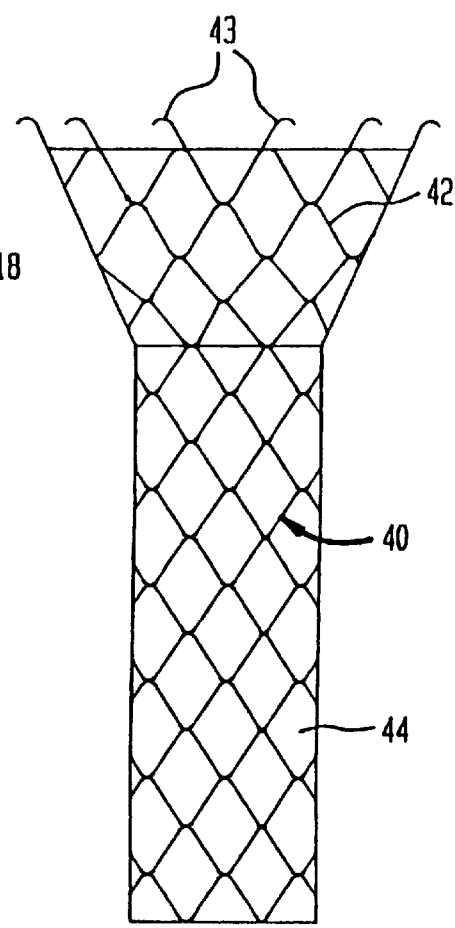

In cases where it is required to implant a prosthesis in the other common iliac artery a second prosthesis comprising a second stent 40 as shown in FIG. 1b can be used. The second stent 40 includes a wire skeleton comprising a proximal frustoconical part 42 and a distal part 44. The distal part 44 of the second stent 40 also may be covered with a tubular graft layer of a biocompatible fabric such, for example, as polyester or polytetrafluoroethylene fabric (FIGS. 5, 6, and 7).

The frustoconical proximal part 42 is constructed in the same way as the frustoconical parts 14, 18 of the bifurcated stent 10; the distal part 44 is constructed in the same way as the distal part 16 of the bifurcated stent 10. The distal end of the frustoconical proximal part 42 is secured to the proximal end of the distal part 44 by securing juxtaposed apices using polypropylene filaments as described above.

In use, the second prosthesis is compressed radially inwards and is received in a catheter for percutaneous or "cut down" delivery to the other common iliac artery. The frustoconical proximal part 42 is guided, in the radially compressed state, into the second frustoconical part 18 of the bifurcated stent 10. The catheter is then withdrawn allowing the second stent 40 to re-expand towards its remembered configuration, until the distal part 14 engages the endoluminal surface of the other common iliac artery, and the outer surface of the frustoconical proximal part 42 engages the interior surface of the second frustoconical part 18 of the bifurcated stent 10.

As with other stents described herein, the frustoconical proximal part 42 may be formed with circumferentially spaced barbs or hooks 43, as shown in FIG. 1b, which engage in the wire skeleton of the second frustoconical part 18 of the bifurcated stent 10. When barbs 43 are on proximal portion 12, they engage the inner wall of the artery.

The tapered configurations of the second frustoconical part 18 of the bifurcated stent 10 and of the proximal frustoconical part 42 of the second stent 40 are such that in the fitted position as described, the prosthesis are locked together to resist longitudinal separation in service. Barbs or hooks on the second stent 40 and/or an frustoconical proximal part 42 help to resist such longitudinal separation.

In another example of the present invention a bifurcated endoluminal prosthesis 50 as shown in FIG. 5 includes a bifurcated stent comprising a proximal portion 52 which tapers radially inwardly from its proximal end 54 to its distal end 56, and first and second transversely spaced frustoconical distal portions 58, 60 which are secured to the distal end 56 of the proximal portion 52; the proximal portion 52 is covered with a tubular graft layer of a biocompatible fabric 62.

In use the prosthesis is delivered percutaneously or by "cut down" methods to an artery in juxtaposition with an arterial bifurcation; blood can flow through the frustoconical proximal portion 52 into each of the branched arteries through the first and second distal frustoconical portions 58, 60. If a prosthesis is required in one or both of the branched arteries, a separate prosthesis comprising a stent of the type shown in FIG. 1b referred to above covered with fabric can be connected to the bifurcated prosthesis 50 by inserting and re-expanding the proximal end of such a separate prosthesis in one or both of the distal frustoconical portions 58, 60 of the prosthesis 50 for engagement therein.

Another variant of the present invention is shown in FIG. 6 which shows a bifurcated endoluminal prosthesis 70 having a proximal portion 72 which is secured at its distal end 74 to two transversely spaced frustoconical intermediate portions 76, 78.

One of said frustoconical intermediate portions 76 is secured at its distal end to an elongate distal portion 80. The proximal end 82 of the proximal portion 72 is flared radially outwards towards its proximal end 82 to engage the intraluminal surface of the host blood vessel in service. Save for this flared portion, the entire endoprosthesis is covered with a fabric graft layer as shown in FIG. 6; said graft layer is carried externally of the wire skeleton and is folded over the distal extremity 84 of the other frustoconical intermediate portion 78 to form an internal lining in said other frustoconical immediate portion 78.

Said other frustoconical intermediate portion 78 constitutes a female cooperating portion in accordance with the present invention which is adapted to receive a male engaging portion of another prosthesis as indicated at 86 in FIG. 6. Said other prosthesis 86 includes a frustoconical proximal portion 88 which constitutes the male engaging portion and an elongate distal portion 90. The whole of the other prosthesis 86 is covered with a fabric graft layer as shown in FIG. 6. In service, the male engaging portion 88 of the other prosthesis 86 is entered into and engaged with the female cooperating portion 78 of the bifurcated prosthesis 70 in situ in the manner herein before described. The fabric layer on the male engaging portion 88 butts face-to-face on the folded over portion of the fabric layer disposed internally of the female cooperating portion 78 to form a substantially blood-tight seal therewith.

Yet another example of the present invention is shown in FIG. 7 in which a bifurcated endoluminal prosthesis 91 has a generally cylindrical proximal portion 92; said proximal portion 92 is connected at its distal end 93 to an elongate, generally cylindrical distal portion 94. Said proximal portion 92 is also connected at its distal end 93 to a generally cylindrical intermediate portion 95 which is secured in transversely spaced relation to the elongate distal portion 94. Said cylindrical intermediate portion 95 constitutes a female engaging portion which is adapted to receive a generally cylindrical male engaging portion of a second elongate prosthesis (not shown). The male engaging portion is equipped with circumferentially spaced external barbs to engage in the female cooperating portion in service. As shown in FIG. 7, the whole of the bifurcated prosthesis 91 is covered with an external fabric graft layer save for a flared portion 96 towards the proximal end 97 of the proximal portion 92.

Referring to FIGS. 8(a)–8(f), an exemplary embodiment of a delivery system according to the present invention will be described. This system is used to deploy the bifurcated stent 10 when it is covered with a fabric graft layer to create an endoluminal prosthesis. Introducer 100 includes outer sheath 101. Outer sheath 101 is a cylindrical tube adapted to be inserted either percutaneously or by "cut-down" procedures into the vasculature from an entry point to the bifurcation site where the prosthesis is to be deployed.

Housed within outer sheath 101 is proximal portion pusher 102. Proximal portion pusher 102 is a cylindrical tube having an outside diameter smaller than the inside diameter of outer sheath 101. Proximal portion pusher 102 is preferably slidable throughout the length of outer sheath 101.

Disposed within proximal portion pusher 102 is distal portion pusher 103. Distal portion pusher 103 is a cylindrical tube slidably contained within distal portion pusher 102. Distal portion pusher 103 is preferably adapted to slide throughout the entire length of proximal portion pusher 102.

Disposed within distal portion 103 is balloon catheter 104. Balloon catheter 104 is adapted to slide within distal portion pusher 103. At the leading end 105 of balloon catheter 104 is nose cone 106. Balloon 107 is attached to balloon catheter 104 between nose cone 106 and proximal end 115 of proximal portion pusher 102.

As shown in FIG. 8(g), which is a cross-sectional view of balloon catheter 104 in the direction A—A of FIG. 8(f), balloon catheter 104 has a guide wire conduit 104a. Guide wire conduit 104a extends throughout the length of balloon catheter 104 for passing a guide wire (not shown) through introducer 100. In the illustrated embodiment, balloon catheter 104 also includes injection orifice 109 and an injection conduit 109a. Injection conduit 109a connects injection orifice 109 to an injection site 108 at or near the distal end of balloon catheter 104 as shown in FIG. 8(e). Radiopaque liquid may be injected into infection site 108, through injection conduit 109a, out injection orifice 109, and into the vasculature to monitor deployment of the prosthesis.

Also in the illustrated embodiment of FIGS. 8(f) and 8(g), balloon catheter 104 has an inflation orifice 110 located at a point where balloon 107 is attached to balloon catheter 104. A balloon inflation conduit 110a connects balloon inflation orifice 110 to balloon inflation site 111 (FIG. 8(e)). Balloon 107 may be inflated and deflated from balloon inflation site 111 during delivery of the prosthesis.

In an alternative embodiment illustrated in FIG. 9, seals 150, 151 may be disposed around the distal ends 160, 161 of outer sheath 10 and proximal portion pusher 102. Seals 150, 151 may be formed of silicone tubes.

Figure 10A:
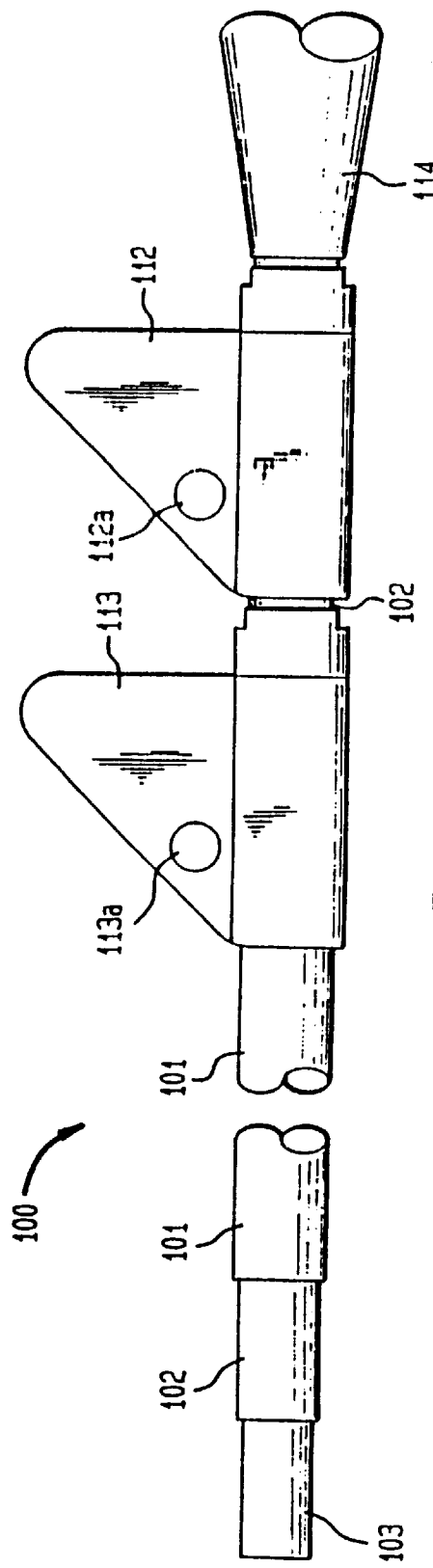
FIGS. 10(a) and 10(b) are side views of other alternative embodiments of an introducer according to the present invention.

FIG. 10(a) shows an alternative embodiment of introducer 100. As shown in FIG. 10(a), wings 112 and 113 are provided at the distal end of introducer 100. Wing 112 is connected to proximal portion pusher 102, and wing 113 is connected to outer sheath 101. Wings 112 and 113 indicate the rotational orientation of proximal portion pusher 102 and outer sheath 101, respectively. This in turn indicates the orientation of proximal portion 12 within outer sheath 101 and distal portion 16 within proximal portion pusher 102. Wings 112 and 113 in the illustrated embodiment are also provided with holes 112a and 113a.

Figure 10B:
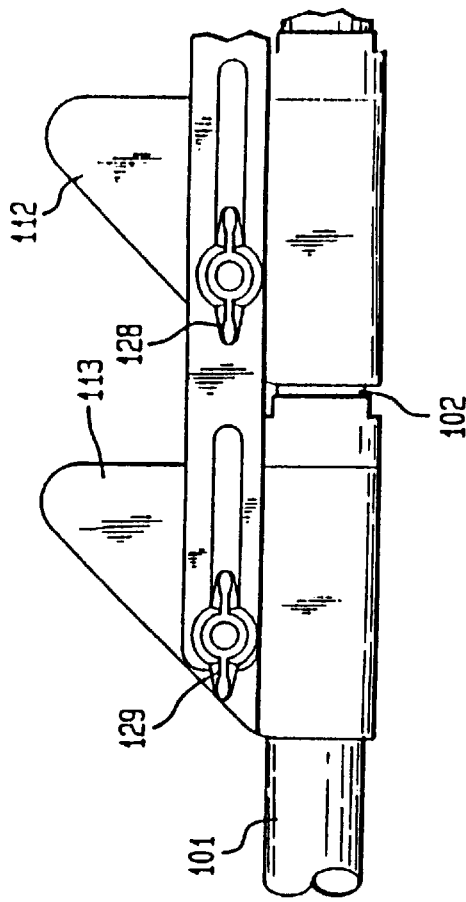

As shown in FIG. 10(b), a rod 128 or other fixation device may be attached to wings 112 and 113 using e.g. bolts through holes 112a and 113a secured by wing nuts 129 or other securing means. Rod 128 prevents relative movement of proximal portion pusher 102 and cuter sheath 101. Wings may also be provided on distal portion pusher 103 and used to secure distal portion pusher 103 to either proximal portion pusher 102 or outer sheath 101 using a fixation device as described above.

Also shown in FIG. 10(a) as part of introducer 100 is hemostasis valve 114. Hemostasis valve 114 is connected to distal portion pusher 103 and acts as a simple seal around balloon catheter 104. Although it prevents fluid loss, hemostasis valve 114 allows balloon catheter 104 to slide within distal portion pusher 103. Alternatively, a Touhy-Borst valve (not shown) may be used instead of hemostasis valve 114. The Touhy-Borst valve is a device that may be manually tightened over balloon catheter 104. Lightly tightening such a valve permits balloon catheter 104 to slide; firmly tightening such a valve clamps balloon catheter 104 in place.

In use, the prosthesis must first be loaded into introducer 100. Outer sheath 101 is first removed from introducer 100. Balloon catheter 104 is then threaded through distal portion 16 and proximal portion 12 of the prosthesis. The prosthesis is then cooled to a temperature of approximately 10° C. or below and radially compressed. For this purpose, the prosthesis may be immersed in cold water. The prosthesis should preferrably remain in the water during the loading operation.

As supporting stent 10 is compressed beneath the fabric covering of the prosthesis, excess fabric is produced. This excess fabric may simply be pinched together and laid over the compressed prosthesis in longitudinal folds.

Distal portion 16 of the prosthesis in the radially compressed state is then inserted into proximal portion pusher 102. Outer sheath 101 is then pulled over proximal portion 12 of the prosthesis and over proximal portion pusher 102. A thread (not shown) may be attached to the proximal end of proximal portion 12 of the prosthesis and threaded through outer sheath 101. This thread may then be used to pull proximal portion 12 through outer sheath 101. During the loading process, it is important to keep proximal portion 12 and distal portion 16 of the prosthesis properly aligned with outer sheath 101 and proximal portion pusher 102. Marks may be placed on the outside of outer sheath 101 and proximal portion pusher 102 to ensure proper alignment.

Referring again to FIG. 8(f), the prosthesis is inserted such that the outer surface of proximal portion 12 contacts and is radially restrained by outer sheath 101, and the outer surface of distal portion 16 contacts and is radially restrained by proximal portion pusher 102. End 115 of proximal portion pusher 102 longitudinally engages proximal portion 12 of the prosthesis as shown in FIG. 8(f).

Balloon catheter 104 is positioned such that nose cone 106 just clears proximal end 117 of outer sheath 101. The introducer is now in condition for insertion into the patient.

Referring to FIG. 11, introducer 100 is passed through an entry point (not shown) either in the patient's skin (percutaneous operation) or into the vasculature itself which has been surgically exposed ("cut-down" operation). Introducer 100 is inserted over a guide wire 170 into the vasculature from the entry point to the desired delivery location at an angeological bifurcation.

In the aorta, introducer 100 is positioned such that end 117 of outer sheath 101 is approximately level with renal arteries 180 as shown in FIG. 11. Balloon catheter 104 is then extended while maintaining outer sheath 101 in a fixed position. Balloon catheter 104 in this embodiment is extended until distal end 105 of nose cone 106 is approximately 35 mm above the proximal tip 117 of outer sheath 101. Then, while maintaining proximal portion pusher 102 in a fixed position, outer sheath 101 is withdrawn until the proximal tip of the prosthesis is level with proximal tip 117 of outer sheath 101. It will be noted that balloon catheter 104 does not move while outer sheath 101 is so withdrawn.

Introducer 100 is then repositioned to place the prosthesis in the desired deployment location. Proper placement may be facilitated with the use of radiopaque markers as described above. Balloon catheter 104 is then extended such that balloon 107 is above renal arteries 180. Balloon 107 is then inflated to occlude the aorta as shown in FIG. 12.

Figure 13:
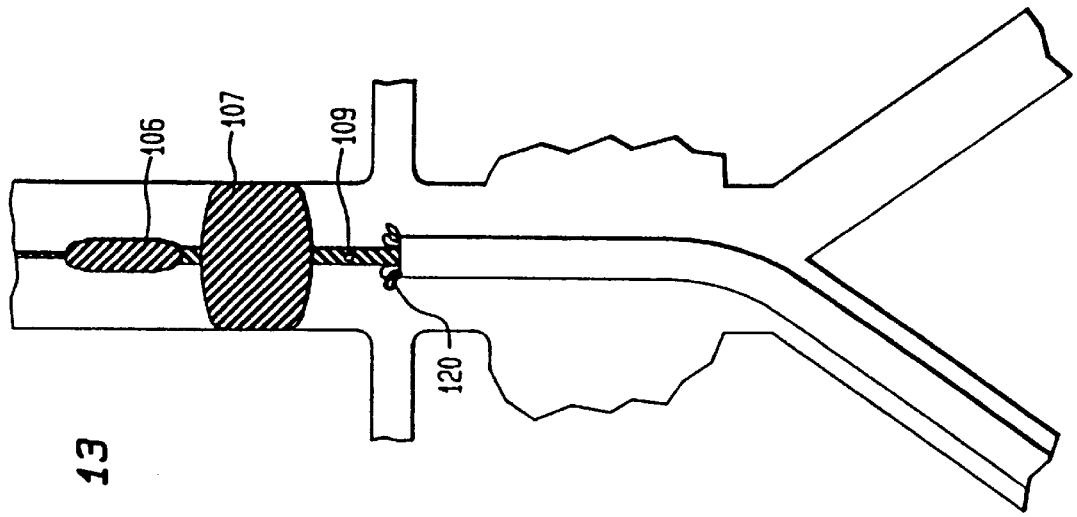

While maintaining proximal portion pusher 102 in a fixed position, outer sheath 101 is withdrawn until the proximal end of the prosthesis emerges from outer sheath 101 as shown in FIG. 13. Using a radiopaque marker 120 disposed on proximal end of the prosthesis, the introducer is rotated until proper alignment of the prosthesis is obtained. In the illustrated embodiment, radiopaque marker 120 is a platinum wire twisted around an apex of the prosthesis in a "V" shape. To ensure proper alignment, the stent should be rotated until only the profile of the V is seen and shows up as a straight line rather than a "V".

Figure 14:
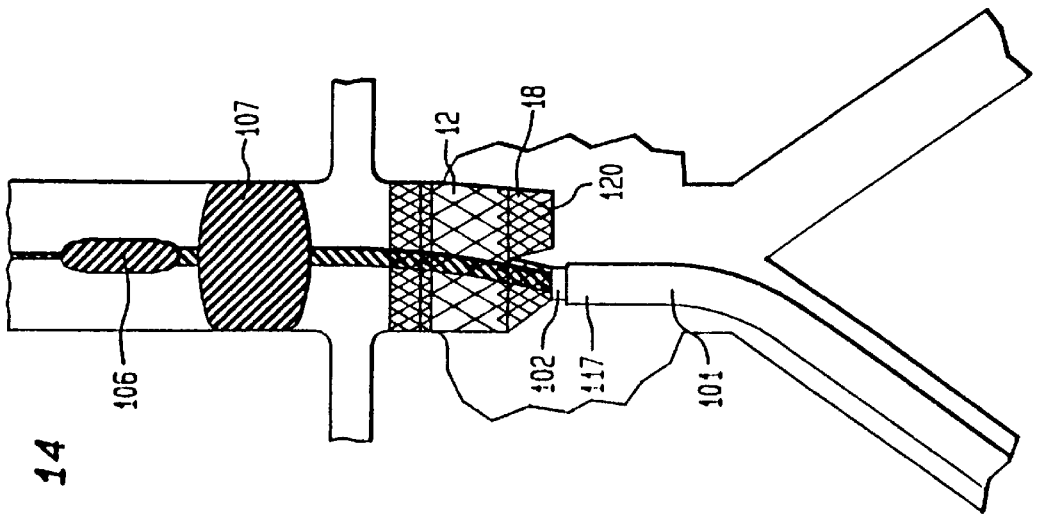

Outer sheath 101 is further withdrawn while maintaining proximal portion pusher 102 fixed until proximal portion 12 is fully deployed from the end of outer sheath 101, and the frustoconical portion 1a of the prosthesis just clears end 117, as shown in FIG. 14.

Figure 15:
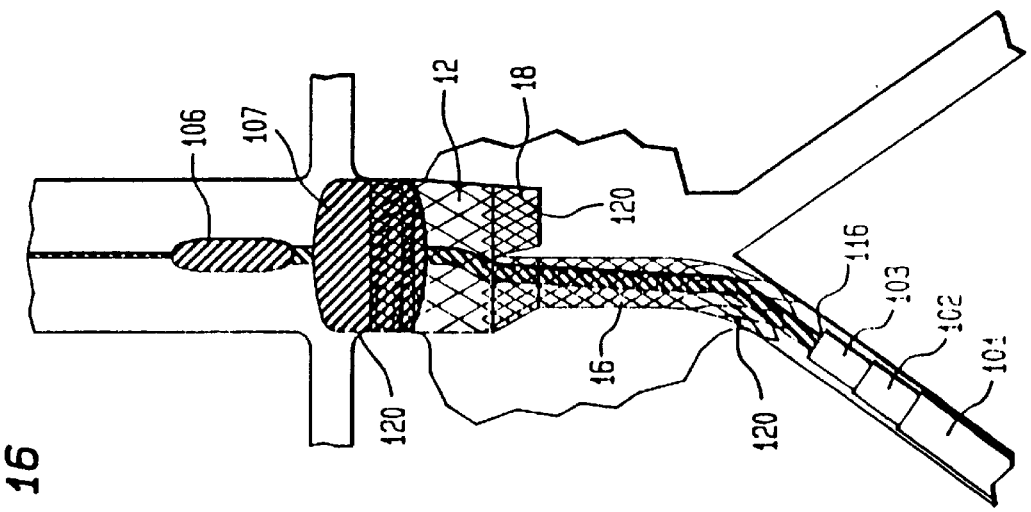

Balloon 107 is then deflated to allow blood to flow through proximal portion 12 and out frustoconical portion 18 of the prosthesis. Balloon 107 is withdrawn into the prosthesis until the distal end 118 of nose cone 106 is just above the proximal end of the prosthesis. Balloon 107 is then inflated to seat the prosthesis, which may be provided with barbs (not shown) at its proximal end, against the wall of the aorta, as shown in FIG. 15.

Figure 16:
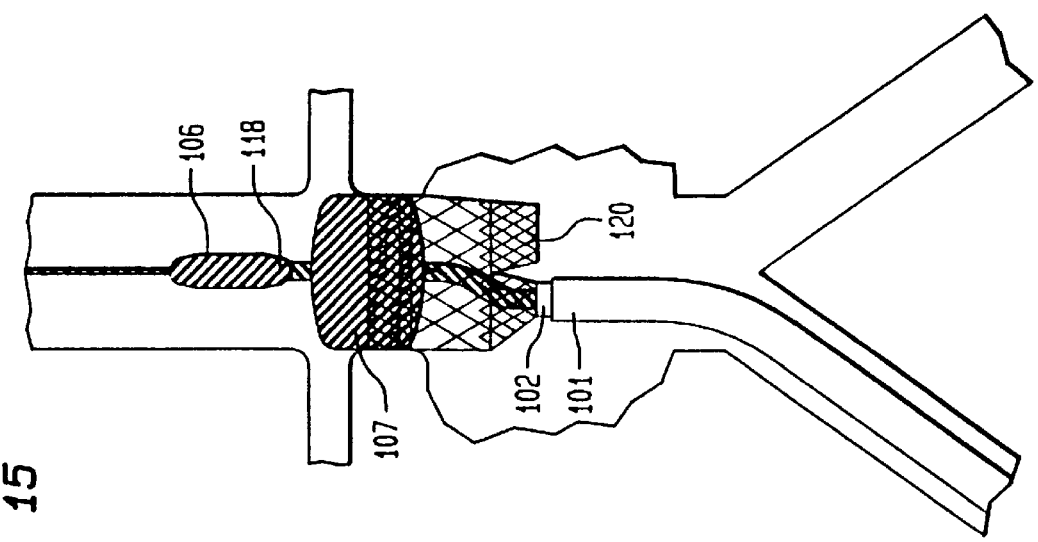
Figure 17:
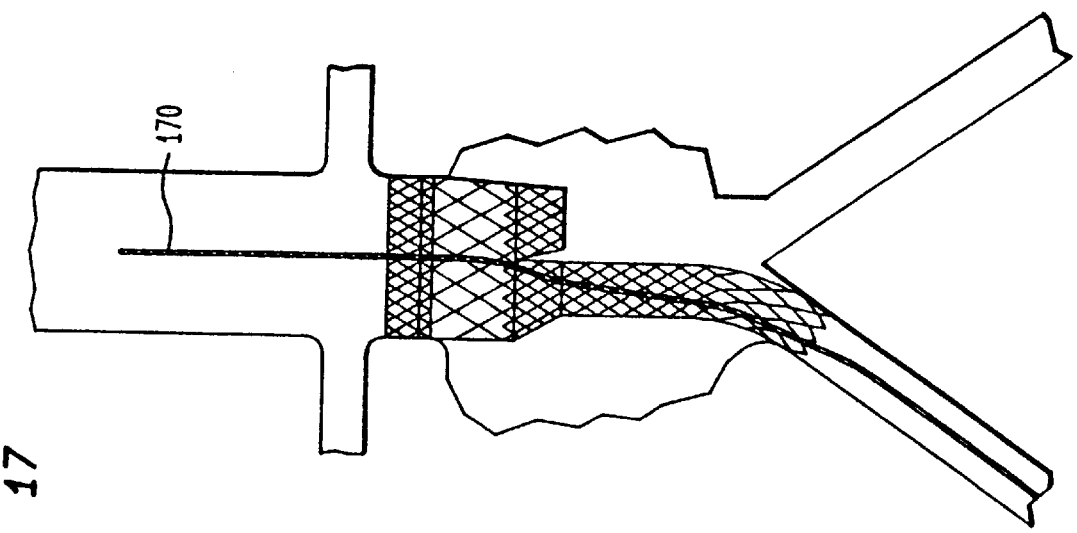

Distal portion pusher 103 is then maintained in a fixed position while outer sheath 101 is withdrawn. Once outer sheath 101 has been withdrawn to the point at which proximal end 117 of outer sheath 101 is flush with proximal end 115 of proximal portion pusher 102, both outer sheath 101 and proximal portion pusher 102 are withdrawn, still maintaining distal portion pusher 103 in a fixed position. Outer sheath 101 and proximal portion pusher 102 are withdrawn until distal portion 16 of the prosthesis is deployed clear of proximal end 116 of distal portion pusher 103 as shown in FIG. 16. Balloon 107 is slowly deflated to allow blood flow to be established through the proximal portion 12 of the prosthesis and out through frustoconical portion 18. Balloon 107 may be used to model distal portion 16 of the prosthesis as necessary by inflating balloon 107 where needed to expand distal portion 16. Balloon 107 is then deflated, and introducer 100 is withdrawn from the vasculature, leaving the guide wire 170 in place, as shown in FIG. 17.

FIG. 21(a) illustrates an exemplary second introducer 300 used for deploying second distal part 44. Second introducer 300 of the illustrated embodiment comprises cylindrical outer sheath 301 and female Luer lock assembly 310. Second introducer 300 also has hemostasis valve 361 contained within a hub 362 thereof. Cartridge 311 shown in FIG. 21(b) is adapted to be attached to second introducer 300. Cartridge 311 has threaded male Luer lock assembly. 312 provided on its proximal end. Cartridge 311 has outer tube 313 which houses inner tube 314.

In use, a thin-walled tube (not shown) is first threaded through distal portion 44. This tube serves as a guide wire guide, allowing a guide wire to be threaded straight through distal portion 44 as discussed below. Distal portion 44 containing the thin-walled tube is then cooled, radially compressed, and inserted into inner tube 314 of cartridge 311 in a manner similar to that described for inserting the bifurcated prosthesis into proximal portion pusher 102 and outer sheath 101. When distal portion 44 has been loaded into inner tube 314 of cartridge 311, the thin-walled tube serving as a guide wire guide extends out both ends of cartridge 311.

Figure 18:
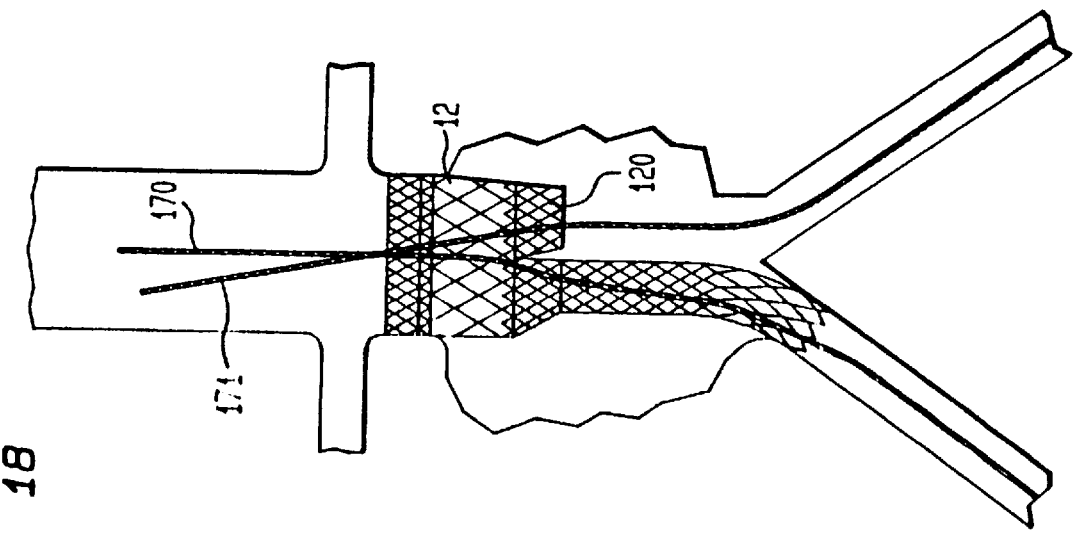

A guide wire 171 is then inserted into the vasculature to the bifurcation site and through distal stent portion 12 as shown in FIG. 18. A dialator 359 (FIG. 21(c)) having an outer diameter slightly less than the inner diameter of second introducer 300 is then inserted into second introducer 300 such that tapered end 360 extends out end 320 of second introducer 300. End 360 of dialator 359 has a hole therein that is just slightly larger than guide wire 171 and tapers gradually outward from the hole to the outer diameter of dialator 359.

Figure 19:
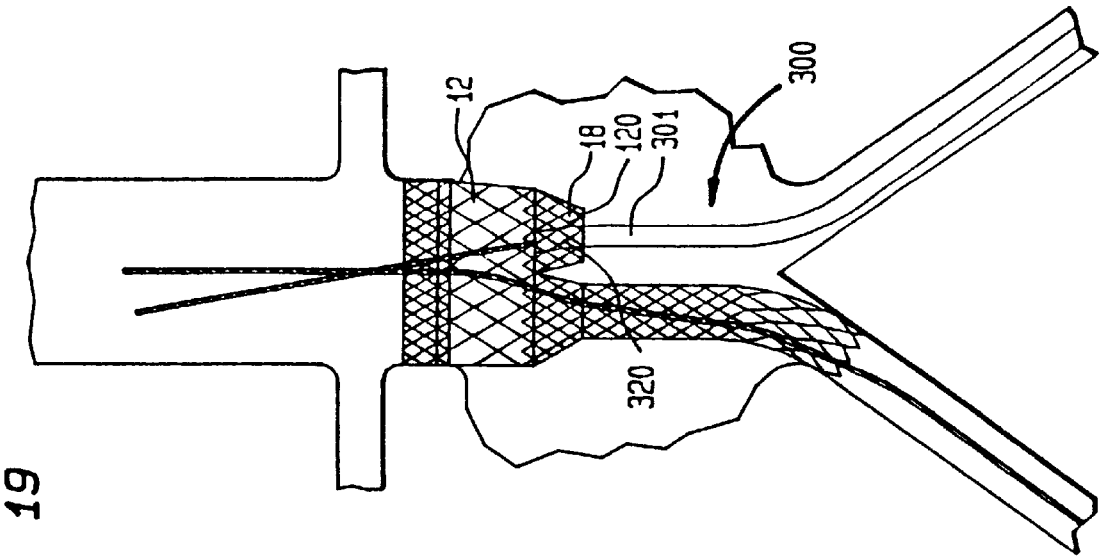

Second introducer 300 is then inserted into the vasculature over guide wire 171 by passing guide wire 171 into and through dialator 359. Dialator 359 with tapered end 360 provides a smooth transition within the blood vessel from the diameter of guide wire 171 to the diameter of second introducer 300. Second introducer 300 is maneuvered such that outer sheath 301 is inside frustoconical portion 18 of proximal portion 12 by at least 20 mm in this embodiment, as shown in FIG. 19. Dialator 359 is then removed from second introducer 300 and from the vasculature and is discarded.

Cartridge 311 is then passed over guide wire 171 by passing guide wire 171 through the thin-walled guide wire guide within distal portion 44 contained in cartridge 311. The guide wire guide is then removed and discarded.

Cartridge 311 is then lockingly engaged with introducer 300 by mating male Luer lock assembly 310 with female Luer lock assembly 312. Such locking engagement prevents relative movement of cartridge 311 and introducer 300. Preventing relative movement lends stability and reliability to the insertion process that has not heretofore been achieved.

A pusher 315 is then inserted into inner tube 314 of cartridge 311 such that proximal end 317 of pusher 315 longitudinally contacts a distal end of distal portion 44 within inner tube 314. Pusher 315 pushes distal portion 44 through cartridge 311 and into outer sheath 301 of introducer 300. Distal portion 44 is pushed through outer sheath 301, which remains in a fixed position, until distal portion 44 is at proximal end 320 of outer sheath 301 (see FIG. 19). Again, radiopaque markers 120 may be used to align distal portion 44 properly with proximal portion 12.

Pusher 302 is held firmly in place, and outer sheath 301 is withdrawn approximately 2 cm. This deploys frustoconical part 42 of distal part 44 inside the frustoconical part 18 as shown in FIG. 19. The outer surface of frustoconical part 42 engages the inner surface of frustoconical part 18 such that distal portion 44 is connected to proximal portion 12 to resist longitudinal separation.

Figure 20:
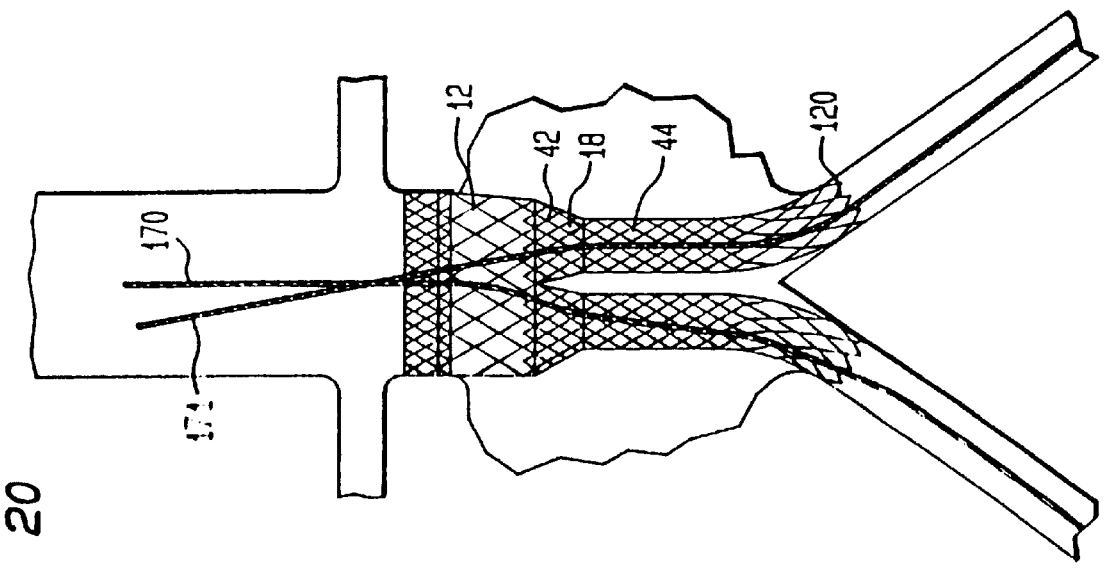

Outer sheath 301 may then be withdrawn while maintaining pusher 302 in a fixed position to fully deploy distal portion 44, as shown in FIG. 20. If necessary, balloon catheter 104 may be inserted through sheath 301 in order to model distal portion 44. Introducer 301 and guide wires 170, 171 are then removed from the vasculature and the entry points are closed.

The delivery apparatus and method described above are particularly useful in treating an abdominal aortic aneurysm with a bifurcated prosthesis according to the present invention. Other diseases and alternative embodiments of the prosthesis and delivery method will now be described.

In the case of an abdominal aortic aneurysm confined to the aorta and not extending far enough to affect the iliac arteries, a straight (i.e. non-bifurcated) stent may be used. Preferably, for such applications, the straight stent comprises a composite of at least two axially aligned stent segments.

Two embodiments of such straight stents are described herein, each comprising axially aligned stent requests, each of the requests comprising one or more adjacent hoops, perpendicular to a common axis, and each hoop being formed of wire in a sinuous or zigzag configuration with some or all of the juxtaposed apices in adjacent hoops secured to one another.

Figure 22:
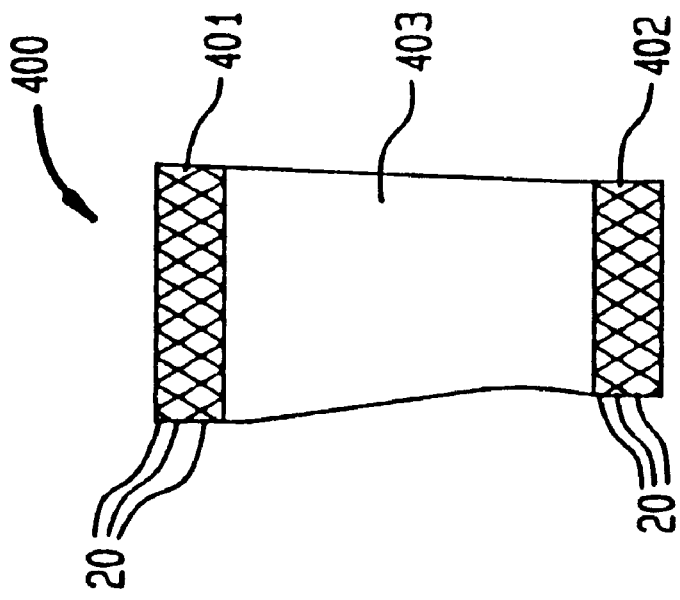

First, referring to FIG. 22, straight stent 400 comprises proximal stent portion (or segment) 401, distal stent portion 402, and an intermediate portion 403.

Proximal portion 401 is a ring formed of a number of longitudinally spaced hoops 20 as described in connection with the formation of stent 10 above. In the illustrated embodiment, two hoops 20 are used, each hoop 20 having a unit width.

Distal portion 402 is also a ring formed of longitudinally displaced hoops 20 in the manner described above. Distal ring 402 has two hoops 20 of unit width in the illustrated embodiment.

Intermediate portion 403 of straight stent 400 is formed of biocompatible woven fabric such as, for example, a plain woven fabric made from 30 or 40 denier polyester. In this embodiment, intermediate fabric section 403 does not cover a stent. Fabric portion 403 is attached at its proximal and distal ends to the proximal and distal stent portions, respectively, by stitching, for example, with 0.003 inch polypropylene filaments around apices 22 of the stent portions. Other than such connections at its longitudinal ends, intermediate fabric section 403 is unsupported by any stent.

Figure 23:
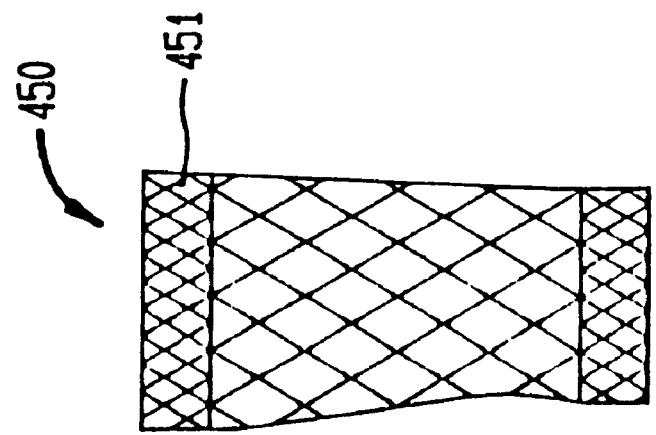
FIGS. 22 and 23 are side views of alternative stents according to the present invention.

The second embodiment of a straight stent that may be used according to this invention is illustrated in FIG. 23. Straight stent 450 includes stent portion 451, constructed of wire loops as described above with reference to stent portions 401 and 402. Stent portion 451 is partially covered by fabric 452. In this embodiment, fabric portion 451 covers and is supported by stent 451, whereas with stent 400, the fabric portion 403 is not supported by a stent.

Figure 24B:
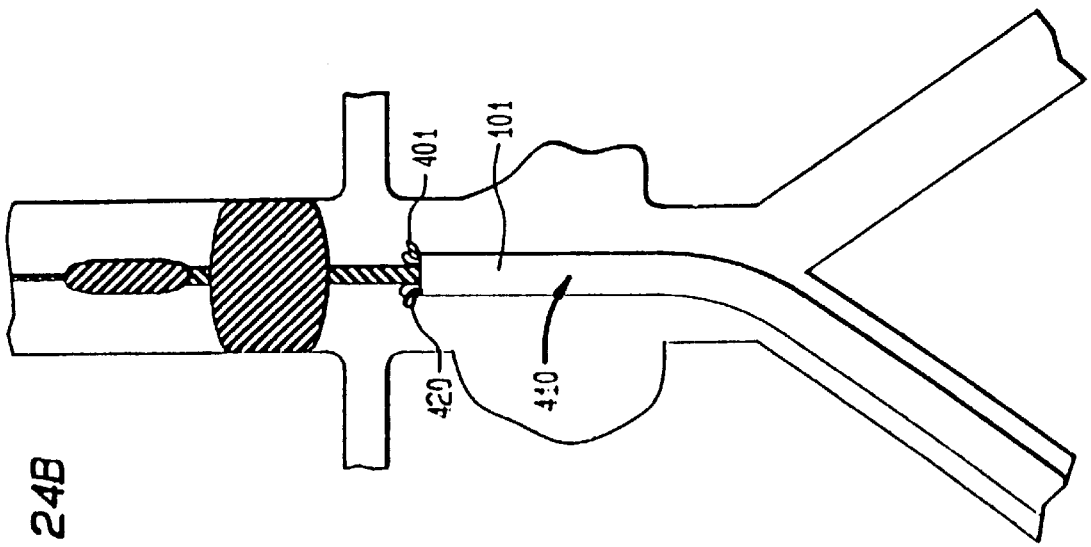
Figure 24A:
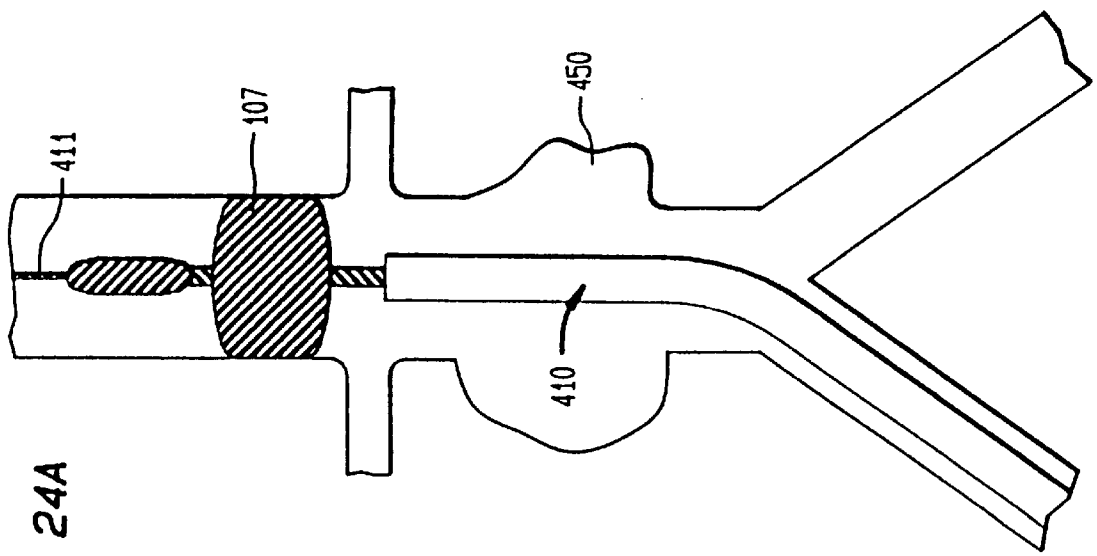

To treat an abdominal aortic aneurysm that does not extend down over the walls of the iliac arteries, as shown in FIG. 24(a), straight stent 400 (or 450) is disposed as illustrated in FIG. 26. Proximal stent portion 401 engages the inner walls of the aorta above the aneurysm. Distal stent portion 402 engages the inner wall of the aorta below the aneurysm. Intermediate fabric portion 403 extends across the aneurysm, providing a strong, stable lumen for blood flow through the aorta.

FIG. 28 illustrates the delivery apparatus used to implant straight stent 400 in the vasculature. This apparatus is very similar to that described above for the delivery system to be used with the bifurcated stent or prosthesis. Accordingly, like reference numerals refer to the same components.

In the introducer 410 shown in FIG. 28, proximal portion pusher 102 engages proximal stent portion 401. Distal portion pusher 103 engages distal stent portion 402.

In use, straight stent 400 is first charged into the introducer by cooling it to temperatures below 10° C., radially compressing it, and inserting it within outer sheath 101, as described above in connection with the bifurcated stent or prosthesis. The remainder of introducer 410 is also assembled as described in connection with introducer 100.

Introducer 410 is passed through an entry point (not shown) over guide wire 411 as shown in FIG. 24(a). This insertion may be accomplished using percutaneous or cut-down techniques. Introducer 410 is then inserted to the desired delivery location.

In the aorta, introducer 410 is positioned and balloon 107 is inflated above the renal arteries in the same manner as described above in connection with the bifurcated stent and as illustrated in FIG. 24(a).

While maintaining proximal portion pusher 102 in a fixed position, outer sheath 101 is withdrawn until proximal portion 401 of stent 400 emerges from outer sheath 101 as shown in FIG. 24(b). Using a radiopaque marker 420 disposed on the proximal end of the proximal portion 401, stent 400 is optimally aligned within the aorta. Outer sheath 101 is further withdrawn until proximal portion 401 emerges therefrom, as shown in FIG. 25. Outer sheath 101 is then further withdrawn until it is flush with proximal portion pusher 102. Then both outer sheath 101 and proximal portion pusher 102 are withdrawn while maintaining distal portion pusher 103 in a fixed position. Distal portion 402 is thus deployed from the end of outer sheath 101, as shown in FIG. 26.

Balloon 107 is then deflated and withdrawn inside proximal portion 401 where balloon 107 is re-inflated to seat the stent 400, as shown in FIG. 27. Balloon 107 is then withdrawn, along with the introducer 410 as described above, and the entry point is closed.

FIG. 29 illustrates the apparatus used to deploy straight stent 450, shown in FIG. 23, of the present invention. This apparatus is very similar to that described above for the delivery system to be used with the bifurcated stent or prosthesis. Accordingly, like reference numerals refer to the same components.

Proximal portion pusher 102 in this embodiment is glued to distal portion pusher 103 such that ends 115 and 116 are flush. These flush ends are adapted to engage stent 450 within outer sheath 101.

In use, straight stent 450 is first charged into introducer 490 by cooling it to temperatures below 10° C., radially compressing it, and inserting it within outer sheath 101, as described above in connection with the bifurcated stent or prosthesis. The remainder of introducer 490 is also assembled as described in connection with introducer 100.

Figure 30:
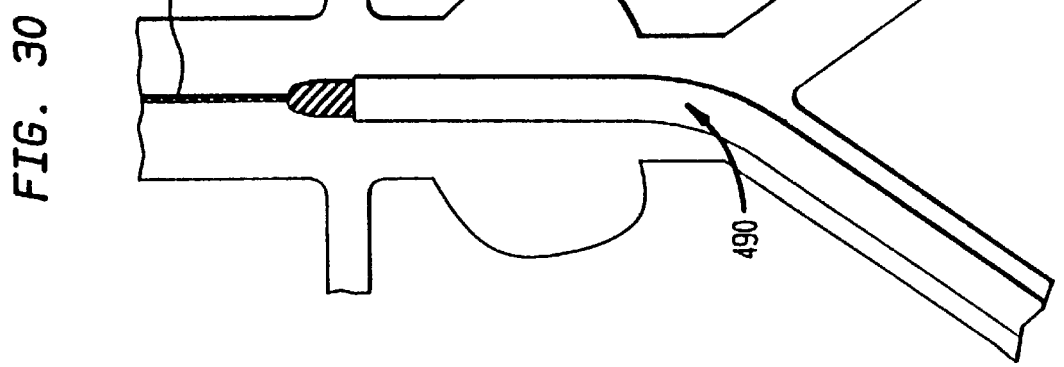

Introducer 490 is passed through an entry point (not shown) over a guide wire 411 as shown in FIG. 30. This insertion may be accomplished using percutaneous or cut-down techniques. Introducer 490 is then inserted to the desired delivery location.

Figure 31:
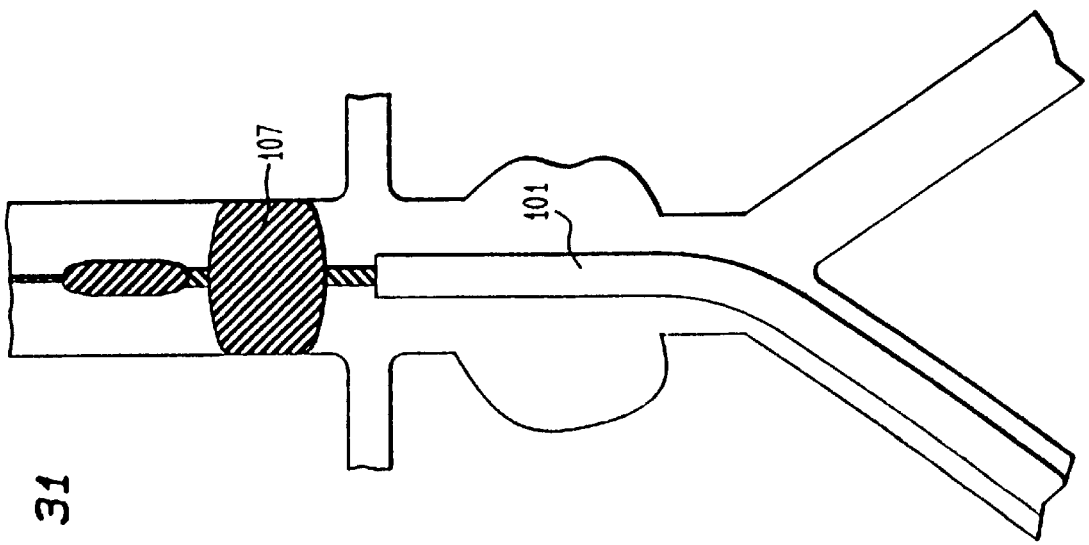
FIGS. 30–34 are sequential cross-sectional views of the bifurcation of the abdominal aortic artery during introduction of an exemplary prosthesis according to the present invention.

In the aorta, introducer 490 is positioned and balloon 107 is inflated above the renal arteries in the same manner as described above in connection with the bifurcated stent and as illustrated in FIG. 31.

Figure 32:
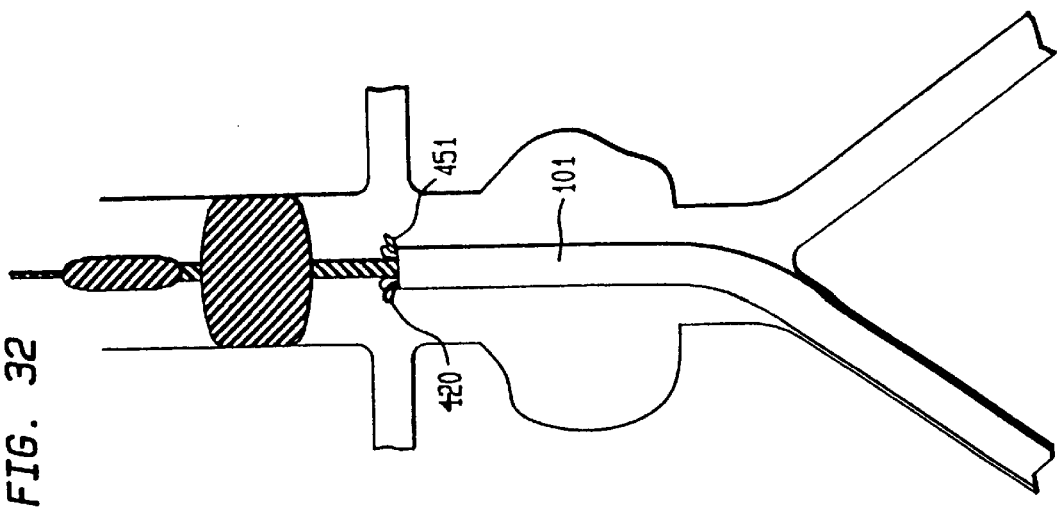
Figure 33:
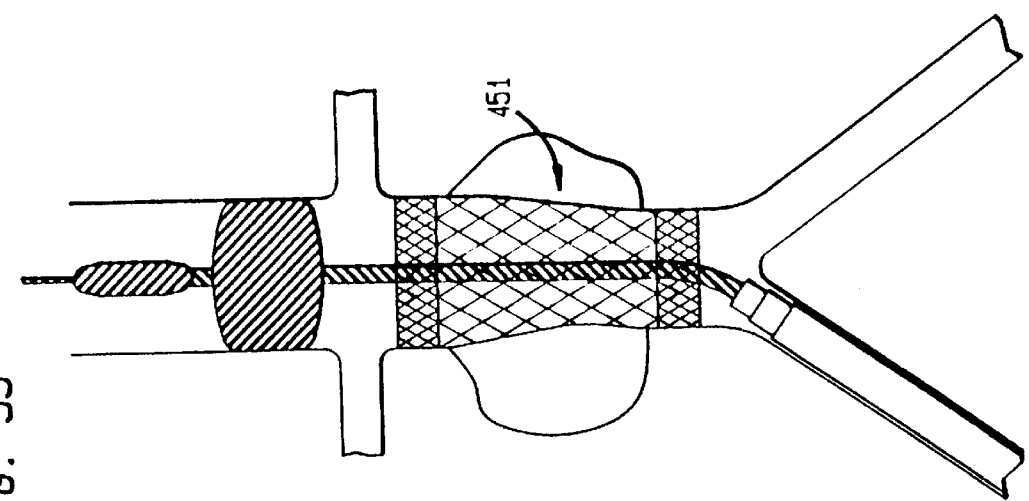

While maintaining attached proximal portion pusher 102 and distal portion pusher 103 in a fixed position, outer sheath 101 is withdrawn until proximal portion 451 of stent 450 emerges from outer sheath 101 as shown in FIG. 32. Using a radiopaque marker 420 disposed on the proximal end of the proximal portion 451, stent 450 is optimally aligned within the aorta. Outer sheath 101 is then completely withdrawn until stent 450 is deployed into the aorta as shown in FIG. 33.

Figure 34:
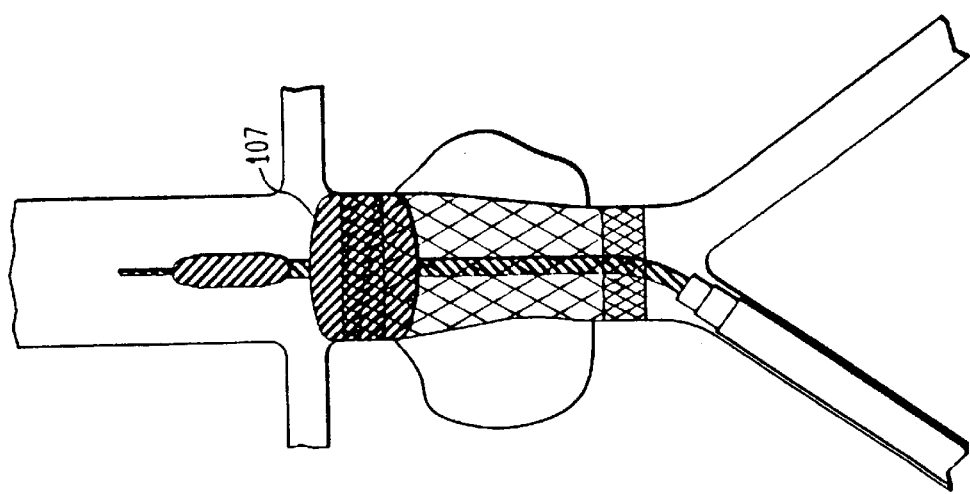

Balloon 107 is then deflated and withdrawn inside proximal portion 451 where balloon 107 is re-inflated to seat the stent 450, as shown in FIG. 34. Balloon 107 is then withdrawn, along with the introducer 490 as described above, and the entry point is closed.

The angeological disease of occlusion is the blockage of an artery resulting from a buildup or clot of soft thrombus. There are two types of occlusions that can occur at the aorta-iliac bifurcation. The first is infrarenal occlusion. In this case, the blockage extends in the aorta from just below the renal arteries into the iliac arteries. The second type is an occlusion that is limited to the immediate area of the bifurcation.

To treat an infrarenal occlusion, a canalization is first made through the thrombus by methods known in the art. A bifurcated endoluminal prosthesis according to the present invention is then implanted at the bifurcation site to provide an unobstructed lumen extending from the aorta into each of the iliac arteries. Blood can thus flow freely from the aorta to the iliac arteries.

The bifurcated endoluminal prosthesis according to the present invention that is used to treat an occlusion must be fabric covered. This is necessary to prevent embolization from the thrombus remaining on the wall of the recanalized artery.

An occlusion at the bifurcation is treated by recanalizing the artery as above. A bifurcated endoluminal prosthesis according to the present invention may be implanted at the bifurcation. Because the occlusion is limited to the immediate bifurcation site, however, the proximal portion of the prosthesis may be shorter than that discussed above.

To implant the bifurcated endoluminal prosthesis to treat both types of occlusion, the delivery system comprising introducer 100 discussed above for delivering the bifurcated endoluminal prosthesis to treat an abdominal aortic aneurysm is used. The same delivery method discussed above for implanting the bifurcated endoluminal prosthesis to treat abdominal aortic aneurysms is used to implant the device to treat the occlusion.

Using the method and apparatus of this invention to treat occlusion provides an unobstructed lumen through which blood can flow from the aorta to the iliac arteries.

The angeological disease of stenosis is a narrowing of an artery caused by a buildup of hard calcified plaque. This is usually caused by a buildup of cholesterol. To treat such an angeological disease, angioplasty is performed on the plaque according to methods well known in the art. The bifurcated endoluminal stent according to the present invention is then implanted at the bifurcation site. This stent is the same as that described above for treatment of an abdominal aortic aneurysm. To treat the stenosis, however, it is not necessary to cover the stent with a fabric, thus creating a prosthesis. Because restenosis is rare at the bifurcation site, there is no need to isolate the blood flowing in the lumen from the walls of the arteries.

The delivery system used to implant the bifurcated endoluminal stent used to treat stenosis is the same as that illustrated in FIG. 8 except that balloon 107 is not required. Because there is no fabric around the stent to be affected by blood flow in the arteries and cause migration of the bifurcated stent, it is not necessary to block the blood flow with the balloon. Otherwise, the delivery system for implanting the bifurcated stent to treat stenosis is the same as that for implanting the bifurcated prosthesis to treat abdominal aortic aneurysm.

Similarly, with the exception of the steps involving inflation of balloon 107 to block blood flow, the method of delivering the bifurcated endoluminal stent to treat stenosis is the same as that described above for delivering the bifurcated endoluminal prosthesis to treat abdominal aortic aneurysm.

What is claimed:

1. A stent joining means for joining a first endoluminal stent to a second endoluminal stent to define a continuous lumen through the first and second endoluminal stents, said stent joining means comprising:

a male engaging portion on said first endoluminal stent which has an outer surface and can be compressed radially inwardly, wherein said male engaging portion is flared radially outwardly towards a proximal end; and a female portion on said second endoluminal stent cooperating with said male engaging portion, said female portion having an inner surface;

wherein said first endoluminal stent and said second endoluminal stent consist of a shape memory alloy and the male engaging portion can be entered into the female portion in a radially compressed state and thereafter expanded in the female portion and wherein said outer surface of the male engaging portion and said inner surface of the female portion are inter-engaged to resist longitudinal movement to prevent separation of the first and second endoluminal stents in service.

2. A stent joining means for joining a first endoluminal stent to a second endoluminal stent to define a continuous lumen through the first and second endoluminal stents, said stent joining means comprising:

a male engaging portion on said first endoluminal stent which has an outer surface and can be compressed radially inwardly; and a female portion on said second endoluminal stent cooperating with said male engaging portion, said female portion having an inner surface, wherein the female portion is tapered radially inwardly towards a distal end;

wherein said first endoluminal stent and said second endoluminal stent consist of a shape memory alloy and the male engaging portion can be entered into the female portion in a radially compressed state and thereafter expanded in the female portion and wherein said outer surface of the male engaging portion and said inner surface of the female portion are inter-engaged to resist longitudinal movement to prevent separation of the first and second endoluminal stents in service.

3. A stent joining means for joining a first endoluminal stent to a second endoluminal stent to define a continuous lumen through the first and second endoluminal stents, said stent joining means comprising:

a male engaging portion on said first endoluminal stent which has an outer surface and can be compressed radially inwardly, wherein the male engaging portion comprises a frustoconical wall flaring outwardly towards a longitudinal extremity; and a female portion on said second endoluminal stent cooperating with said male engaging portion, said female portion having an inner surface;

wherein said first endoluminal stent and said second endoluminal stent consist of a shape memory alloy and the male engaging portion can be entered into the female portion in a radially compressed state and thereafter expanded in the female portion and wherein said outer surface of the male engaging portion and said inner surface of the female portion are inter-engaged to resist longitudinal movement to prevent separation of the first and second endoluminal stents in service.

4. A stent joining means for joining a first endoluminal stent to a second endoluminal stent to define a continuous lumen through the first and second endoluminal stents, said stent joining means comprising:

male engaging portion on said first endoluminal stent which has an outer surface and can be compressed radially inwardly; and a female portion on said second endoluminal stent cooperating with said male engaging portion, said female portion having an inner surface, wherein the female portion comprises a frustoconical wall tapering radially inwardly towards a longitudinal extremity;

wherein said first endoluminal stent and said second endoluminal stent consist of a shape memory alloy and the male engaging portion can be entered into the female portion in a radially compressed state and thereafter expanded in the female portion and wherein said outer surface of the male engaging portion and said inner surface of the female portion are inter-engaged to resist longitudinal movement to prevent separation of the first and second endoluminal stents in service.

5. A stent joining means for adjoining a first endoluminal stent to a second endoluminal stent to define a continuous lumen through the first and second endoluminal stents, said stent joining means comprising:

a male engaging portion on said first endoluminal stent which has an outer surface and can be compressed radially inwardly; and two transversely spaced female portions on said second endoluminal stent, at least one female portion on said second endoluminal stent cooperating with said male engaging portion, said female portion having an inner surface;

wherein said first endoluminal stent and said second endoluminal stent consist of a shape memoru alloy and the male engaging portion can be entered into the female portion in a radially compressed state and thereafter expanded in the female portion and wherein said outer surface of the male engaging portion and said inner surface of the female portion are inter-engaged to resist longitudinal movement to prevent separation of the first and second endoluminal stents in service.

6. A stent joining means as claimed in claim 5, at least one of said stents having a taper to resist longitudinal separation of said stents in service.

7. A stent joining means as claimed in claim 5, at least one of said stents having a flare to engage the body lumen.

8. A stent joining means as claimed in claim 5, further comprising a graft layer associated with said female portion, said male engaging portion providing a substantially blood tight seal with said graft layer.

9. A stent joining means as claimed in claim 5, said male engaging portion being flared when uncompressed.

10. A stent joining means as claimed in claim 5, wherein said second endoluminal stent is adapted to extend across a bifurcation in a blood vessel such that in use a proximal end of said second endoluminal stent is disposed proximally of the bifurcation, one of said female portions of said second endoluminal stent is disposed in a branched blood vessel, and said first endoluminal stent is adapted to extend from the other one of said female portions into another branched blood vessel.

11. A stent joining means as claimed in claim 5, at least one of said stents comprising a plurality of co-axial hoops, each of said hoops comprising a zig zag pattern around the circumference thereof.

12. A stent joining means as claimed in claim 5 wherein one of said two transversely spaced distal female portions is adapted for connection to said male engaging portion of said first endoluminal stent and said one spaced distal female portion and said first and second endoluminal stents, in combination, extend across a bifurcation in a blood vessel into two respective branched blood vessels.

13. An endoluminal prosthesis system adapted to be assembled within a body lumen, said endoluminal prosthesis system comprising proximal and distal prosthesis segments, a male engaging portion on a selected one of said proximal and distal prosthesis segments, and a female portion on another one of said proximal and distal prosthesis segments, said male engaging portion being configured to be positioned at least partially within said female portion for inter-engagement between the outer surface of said male engaging portion and the inner surface of said female portion to resist longitudinal movement to prevent separation of said proximal and distal prosthesis segments in service, each of said male engaging portion and said female portion comprising a stent and at least one of said proximal and distal prosthesis segments comprising a graft layer attached to said stent, said graft layer being configured to be interposed between said male engaging portion and said female portion to form a substantially fluid-tight seal upon assembly.

14. A system as claimed in claim 13, said graft layer being attached to said scent of at least one of said prosthesis segments by a filament.

15. A system as claimed in claim 13, said stent of at least one of said prosthesis segments having hoops with a common axis positioned along that axis.

16. A system as claimed in claim 15, each of said hoops comprising a plurality of apices alternately pointing in opposite axial directions, oppositely pointed apices in adjoining hoops abutting one another, at least one pair of said abutting apices being joined by a connecting member.

17. A system as claimed in claim 15, each of said hoops comprising wire disposed in a sinuous or zig zag configuration around the circumference of said hoop, the wire of at least one of said hoops being continuous with the wire of an adjacent hoop.

18. A system as claimed in claim 13, wherein an end portion of said stent of at least one of said prosthesis segments extends beyond said graft layer.

19. A system as claimed in claim 13, at least one of said prosthesis segments comprising barbs or hooks adapted to engage a surrounding body lumen and to resist longitudinal movement or slippage of the segment in service.

20. A system as claimed in claim 13, at least one of said prosthesis segments comprising barbs or hooks to resist longitudinal separation of said prosthesis segments in service.

21. A system as claimed in claim 14, at least one of said prosthesis segments comprising a marker, capable of being imaged from outside of a body in which said prosthesis segment is located, said marker being adapted to facilitate proper alignment or positioning of said prosthesis segment.

22. A system as claimed in claim 21, said marker being adapted to facilitate alignment of said prosthesis segment with the other one of the prosthesis segments.

23. A system as claimed in claim 21, wherein the image of said marker differs depending on the rotational orientation of said prosthesis segment so that said rotational orientation can be determined.

24. A system as claimed in claim 13, at least one of said prosthesis segments having a taper to resist longitudinal separation of said prosthesis segments in service.

25. A system as claimed in claim 13, at least one of said prosthesis segments having a flare to engage the body lumen.

26. A system as claimed in claim 13, wherein said graft layer is associated with said female portion, said male engaging portion providing a substantially blood tight seal with said graft layer.

27. A system as claimed in claim 13, said male engaging portion being flared when uncompressed.

28. A system as claimed in claim 13, said male engaging portion being compressible and capable of self re-expansion to engage said female portion.

29. A system as claimed in claim 13, wherein said proximal prosthesis segment defines two distal lumens, one of which is adapted to extend across a bifurcation in a blood vessel such that in use a proximal end of said proximal prosthesis segment is disposed proximally of the bifurcation, and a distal end of said proximal prosthesis segment is disposed in one of the branched blood vessels, the other of said distal lumens comprising said female portion and being disposed intermediate said proximal and distal ends of said proximal prosthesis segment, and said male engaging portion is disposed on said distal prosthesis segment and is adapted to mate with said female portion and to extend into the other of said branched blood vessels.

30. A system as claimed in claim 13, said stents comprising coaxial hoops, each of said hoops defining a zig zag pattern around the circumference thereof.

31. An endoluminal prosthesis system adapted to be assembled within a body lumen, said endoluminal prosthesis system comprising proximal and distal prosthesis segments, a male engaging portion on a selected one of said proximal and distal prosthesis segments, and a female portion on another one of said proximal and distal prosthesis segments, said male engaging portion being configured to be positioned at least partially within said female portion for inter-engagement between the outer surface of said male engaging portion and the inner surface of said female portion to resist longitudinal movement to prevent separation of said proximal and distal prosthesis segments in service, each of said male engaging portion and said female portion comprising a stent, a graft layer being provided adjacent said outer surface of said male engaging portion and adjacent said inner surface of said female portion, said graft layer of said male engaging portion being configured to be in face-to-face contact with said graft layer of said female portion to form a substantially fluid-tight seal upon assembly.

32. An endoluminal prosthesis system adapted to be assembled within a body lumen, said endoluminal prosthesis system comprising proximal and distal prosthesis segments, a male engaging portion on a selected one of said proximal and distal prosthesis segments, and a female portion on another one of said proximal and distal prosthesis segments, said male engaging portion being configured to be positioned at least partially within said female portion for inter-engagement between the outer surface of said male engaging portion and the inner surface of said female portion to resist longitudinal movement to prevent separation of said proximal and distal prosthesis segments in service, each of said male engaging portion and said female portion comprising a stent;

at least one of said proximal and distal segments comprising a portion having a different radiopacity from said at least one of said proximal and distal segments, said portion having a radiographic image that is detectable using a detector outside the body, said radiographic image of said portion differing depending on the rotational orientation of said at least one of said proximal and distal segments so that said rotational orientation in the body lumen can be determined, and said portion having said different radiopacity being configured in a "V" shape.

33. A system for joining endoluminal prosthesis segments in a vessel, said system comprising a male engaging portion on a selected one of said endoluminal prosthesis segments and a female portion on another one of said endoluminal prosthesis segments cooperating with said male engaging portion, each of said male engaging portion and said female portion comprising a stent, said male engaging portion being flared radially outwardly towards an end thereof, said male engaging portion can be entered at least partially into said female portion, and inter-engagement between the outer surface of said male engaging portion and the inner surface of said female portion resists longitudinal movement to prevent separation of said endoluminal prosthesis segments in service.

34. A system as claimed in claim 33, at least one of said prosthesis segments comprising a graft layer attached to said stent by a filament.

35. A system as claimed in claim 33, said stent of at least one of said male engaging portion and said female portion defining hoops having a common axis and positioned along that axis.

36. A system as claimed in claim 35, said hoops having a plurality of apices alternatingly pointing in opposite axial directions, oppositely pointed apices of adjoining hoops abutting one another, said abutting apices being joined by a connecting member.

37. A system as claimed in claim 35, the configuration of each of said hoops including:
   a plurality of apices disposed about the circumference of said hoop and alternatingly pointing in opposite axial directions; and
   a member which extends, as a single continuous member, from an apex pointed in a first axial direction to the apex of an adjacent hoop pointed in the opposite axial direction.

38. A system as claimed in claim 33, at least one of said prosthesis segments comprising a graft layer, wherein an end portion of said stent of said prosthesis segment extends beyond said graft layer.

39. A system as claimed in claim 33, at least one of said prosthesis segments comprising barbs or hooks adapted to engage a surrounding body lumen and to resist longitudinal movement or slippage of the prosthesis segment in service.

40. A system as claimed in claim 33, at least one of said prosthesis segments comprising barbs or hooks to resist longitudinal separation of said prosthesis segments in service.

41. A system as claimed in claim 33, at least one of said prosthesis segments comprising a radiopaque marker, said radiopaque marker being adapted to facilitate proper alignment or positioning of said prosthesis segment.

42. A system as claimed in claim 41, said radiopaque marker being adapted to facilitate alignment of said prosthesis segment with the other one of said prosthesis segments.

43. A system as claimed in claim 41, wherein the radiographic image of said radiopaque marker differs depending on the rotational orientation of said prosthesis segment so that said rotational orientation can be determined.

44. A system as claimed in claim 33, at least one of said prosthesis segments having a taper to resist longitudinal separation of said prosthesis segments in service.

45. A system as claimed in claim 33, at least one of said prosthesis segments having a flare to engage the body lumen.

46. A system as claimed in claim 33, wherein a graft layer is associated with said female portion, said male engaging portion providing a substantially blood tight seal with said graft layer.

47. A system as claimed in claim 33, said male engaging portion being flared when uncompressed.

48. A system as claimed in claim 33, said male engaging portion being compressible and capable of self re-expansion to engage said female portion.

49. A system as claimed in claim 33, wherein a proximal prosthesis segment defines two distal lumens, one of which is adapted to extend across a bifurcation in a blood vessel such that in use a proximal end of said proximal prosthesis segment is disposed proximally of the bifurcation, and a distal end of said proximal prosthesis segment is disposed in one of the branched blood vessels, the other of said distal lumens comprising said female portion and being disposed intermediate said proximal and distal ends of said proximal prosthesis segment, and said male engaging portion is disposed on a distal prosthesis segment and is adapted to mate with said female portion and to extend into the other of said branched blood vessels.

50. A system as claimed in claim 33, said stent of at least one of said male engaging portion and said female portion comprising a plurality of hoops, each defining a zig zag pattern about the circumference thereof.

51. A system for joining endoluminal prosthesis segments in a vessel, said system comprising a male engaging portion on a selected one of said endoluminal prosthesis segments and a female portion on another one of said endoluminal prosthesis segments cooperating with said male engaging portion, each of said male engaging portion and said female portion comprising a stent, said female portion being tapered radially inwardly towards an end thereof, said male engaging portion can be entered at least partially into said female portion, and inter-engagement between the outer surface of said male engaging portion and the inner surface of said female portion resists longitudinal movement to prevent separation of said endoluminal prosthesis segments in service.

52. An endoluminal prosthesis system adapted to be assembled within a body lumen to provide a continuous lumen, said endoluminal prosthesis system comprising:
   proximal and distal prosthesis segments, said proximal and distal prosthesis segments each comprising a graft layer;
   a male engaging portion on a selected one of said proximal and distal prosthesis segments and a female portion on another one of said proximal and distal prosthesis segments, each of said male engaging portion and said female portion comprising a stent, said male engaging portion being configured to be positioned at least partially within said female portion for contact between the outer surface of said male engaging portion and the inner surface of said female portion, said graft layers of said proximal and distal prosthesis segments together defining a substantially continuous lumen upon assembly of said proximal and distal prosthesis segments, and said graft layer of at least one of said proximal and distal prosthesis segments is configured to be interposed between said male engaging portion and said female portion to form a substantially fluid-tight seal upon assembly.

53. A system as claimed in claim 52, said graft layer of each of said proximal and distal prosthesis segments being attached to a respective one of said stents by a filament.

54. A system as claimed in claim 52, said stent of at least one of said male engaging portion and said female portion comprising a plurality of hoops having a common axis and positioned along that axis.

55. A system as claimed in claim 54, wherein each of said hoops comprises a zig zag or sinuous configuration extending around the circumference of said hoop.

56. A system as claimed in claim 54, each of said hoops comprising a plurality of apices alternately pointing in opposite axial directions, oppositely pointed apices in adjoining hoops abutting one another, at least one pair of said abutting apices being joined by a connecting member.

57. A system as claimed in claim 54, each of said hoops comprising wire disposed in a sinuous or zig zag configuration around the circumference of said hoop, the wire of at least one of said hoops being continuous with the wire of an adjacent hoop.

58. A system as claimed in claim 52, wherein an end portion of at least one of said stents extends beyond a respective one of said graft layers.

59. A system as claimed in claim 52, at least one of said prosthesis segments comprising barbs or hooks adapted to engage a surrounding body lumen and to resist longitudinal movement or slippage of the prosthesis segment in service.

60. A system as claimed in claim 52, at least one of said prosthesis segments comprising barbs or hooks to resist longitudinal separation of said prosthesis segments in service.

61. A system as claimed in claim 52, at least one of said prosthesis segments comprising a radiopaque marker, said radiopaque marker being adapted to facilitate proper alignment or positioning of said prosthesis segment.

62. A system as claimed in claim 61, said radiopaque marker being adapted to facilitate alignment of said prosthesis segment with the other one of said prosthesis segments.

63. A system as claimed in claim 61, wherein the radiographic image of said radiopaque marker differs depending on the rotational orientation of said prosthesis segment so that said rotational orientation can be determined.

64. A system as claimed in claim 52, at least one of said prosthesis segments having a taper to resist longitudinal separation of said prosthesis segments in service.

65. A system as claimed in claim 52, at least one of said prosthesis segments having a flare to engage the body lumen.

66. A system as claimed in claim 52, said male engaging portion providing a substantially blood tight seal with said graft layer associated with said female portion.

67. A system as claimed in claim 52, said male engaging portion being flared when uncompressed.

68. A system as claimed in claim 52, said male engaging portion being compressible and capable of self re-expansion to engage said female portion.

69. A system as claimed in claim 53, wherein said proximal prosthesis segment defines two distal lumens, one of which is adapted to extend across a bifurcation in a blood vessel such that in use a proximal end of said proximal prosthesis segment is disposed proximally of the bifurcation, and a distal end of said proximal prosthesis segment is disposed in one of the branched blood vessels, the other of said distal lumens comprising said female portion and being disposed intermediate said proximal and distal ends of said proximal prosthesis segment, and said male engaging portion is disposed on said distal prosthesis segment and is adapted to mate with said female portion and to extend into the other of said branched blood vessels.

70. A system as claimed in claim 52, said stent of at least one said male engaging portion and said female portion comprising a plurality of co-axial hoops each defining a zig zag pattern.

71. An endoluminal prosthesis system adapted to be assembled within a body lumen to provide a continuous lumen, said endoluminal prosthesis system comprising:

proximal and distal prosthesis segments, said proximal and distal prosthesis segments each comprising a graft layer;

a male engaging portion on a selected one of said proximal and distal prosthesis segments and a female portion on another one of said proximal and distal prosthesis segments, each of said male engaging portion and said female portion comprising a stent, said male engaging portion being configured to be positioned at least partially within said female portion for contact between the outer surface of said male engaging portion and the inner surface of said female portion, a graft layer portion being provided adjacent said outer surface of said male engaging portion and a graft layer portion being provided adjacent said inner surface of said female portion, said graft layer portion of said male engaging portion being configured to be in face-to-face contact with said graft layer portion of said female portion to form a substantially fluid-tight seal upon assembly and to define a substantially continuous lumen upon assembly of said proximal and distal prosthesis segments.

72. A stent joining means for joining a first endoluminal stent to a second endoluminal stent to define a continuous lumen through the first and second endoluminal stents, said stent joining means comprising:

two transversely spaced female portions on said first endoluminal stent, each of said female portions having an inner surface;

a male engaging portion on said second endoluminal stent which has an outer surface and can be compressed radially inwardly, the male engaging portion being configured to be entered into one of the female portions in a radially compressed state and thereafter expanded in the female portion such that the outer surface of the male engaging portion and the inner surface of the female portion are inter-engaged to resist longitudinal movement to prevent separation of the first and second endoluminal stents in service; and a graft layer attached to at least one of said first and second endoluminal stents, said graft layer being configured to be interposed between said male engaging portion and said female portion to form a substantially fluid-tight seal upon assembly.

73. A stent joining means as claimed in claim 72, said graft layer being attached to at least one of said stents by a filament.

74. A stent joining means as claimed in claim 72, at least one of said stents having hoops with a common axis, said hoops being positioned along said axis.

75. A stent joining means as claimed in claim 74, each of said hoops comprising a plurality of apices pointing alternately in opposite axial directions, oppositely pointed apices of adjoining hoops abutting one another, at least some of said abutting apices being joined by a connecting member.

76. A stent joining means as claimed in claim 74, each of said hoops comprising wire disposed in a sinuous or zig zag configuration around the circumference of said hoop, the wire of at least one of said hoops being continuous with the wire of an adjacent hoop.

77. A stent joining means as claimed in claim 72, wherein an end portion of said at least one stent to which said graft layer is attached extends beyond said graft layer.

78. A stent joining means as claimed in claim 72, at least one of said stents comprising barbs or hooks adapted to engage a surrounding body lumen and to resist longitudinal movement or slippage of said stent in service.

79. A stent joining means as claimed in claim 72, at least one of said stents comprising barbs or hooks to resist longitudinal separation of said stents in service.

80. A stent joining means as claimed in claim 72, at least one of said stents comprising at least one marker, imageable from outside a body in which said stent is located, said marker being adapted to facilitate proper alignment or positioning of said stent.

81. A stent joining means as claimed in claim 80, wherein the image of said marker differs depending on the rotational orientation of said stent so that said rotational orientation can be determined.

82. A stent joining means as claimed in claim 80, wherein said marker is adapted to facilitate alignment of said stent with the other of said stents.

* * * * *

UNITED STATES PATENT AND TRADEMARK OFFICE
CERTIFICATE OF CORRECTION

PATENT NO.   : 6,117,167
DATED        : September 12, 2000
INVENTOR(S)  : Goicoechea et al.

It is certified that error appears in the above-identified patent and that said Letters Patent is hereby corrected as shown below:

Column 10,
Line 3, after "14,", change "1a" to -- 18 --.

Column 13,
Line 61, after "and", change "cuter" to -- outer --.

Column 15,
Line 18, after "portion", change "1a" to -- 18 --.

Column 21, claim 5,
Line 14, after "for", change "adjoining" to -- joining --; and
Line 28, after "shape", change "memoru" to -- memory --.

Column 22, claim 14,
Line 19, after "to said", change "scent" to -- stent --; and Column 22, claim 21,
Line 45, after "claim", change "14" to -- 13 --.

Column 23, claim 31,
Line 24, change "portionon" to -- portion on --.

Column 26, claim 69,
Line 48, after "claim", change "53" to -- 52 --.

Signed and Sealed this

Twenty-fifth Day of December, 2001

Attest:

Attesting Officer

JAMES E. ROGAN
Director of the United States Patent and Trademark Office